(12) United States Patent
Lindner et al.

(10) Patent No.: US 6,255,467 B1
(45) Date of Patent: Jul. 3, 2001

(54) HUMAN BLOOD BACTERIUM

(75) Inventors: Luther E. Lindner, College Station; Kathleen MacPhee, Spring, both of TX (US)

(73) Assignee: Pathobiotek Diagnostics Inc., The Woodlands, TX (US)

( * ) Notice: Subject to any disclaimer, the term of this patent is extended or adjusted under 35 U.S.C. 154(b) by 0 days.

(21) Appl. No.: 09/187,946

(22) Filed: Nov. 2, 1998

Related U.S. Application Data

(60) Provisional application No. 60/064,472, filed on Nov. 6, 1997.

(51) Int. Cl.[7] .......................... C07H 21/02; C12P 21/06; C12P 21/04

(52) U.S. Cl. .................... 536/23.1; 536/23.7; 536/24.33; 536/24.3; 435/69.1; 435/71.1

(58) Field of Search ................................. 536/23.1, 23.7, 536/24.33, 24.3; 435/69.1, 71.1

(56) References Cited

PUBLICATIONS

Paul Singleton, Bacteria in Biology, Biotechnology and Medicine, pp. 136–140, 1999, 5th Edition.*
Hiraishi et al Appl Environ Microbiol 61 (6), 2099–2107, 1995.*
Hillier et al genbank Accession T88795, 1995.*
Relman et al Mol Microbiol 6 (13), 1801–1807, 1992.*

* cited by examiner

*Primary Examiner*—Lynette R. F. Smith
*Assistant Examiner*—Li Lee
(74) *Attorney, Agent, or Firm*—Benjamin Aaron Adler

(57) ABSTRACT

The present invention reports a newly-identified human blood bacterium (HBB), provides characterization, culturing and diagnostic methodologies therefor and methods for the treatment of pathophysiological states caused by the bacterium. The bacterium is apparently present in the bloodstream of all humans in very low numbers, and appears to be directly or indirectly associated with several diseases such as chronic fatigue syndrome, multiple sclerosis and other "autoimmune" diseases. Also provided are uses of engineered HBB.

5 Claims, 6 Drawing Sheets

SEQUENCE LISTING

```
<160> NUMBER OF SEQ ID NOS: 20

<210> SEQ ID NO 1
<211> LENGTH: 1208
<212> TYPE: DNA
<213> ORGANISM: unknown
<220> FEATURE:
<221> NAME/KEY: rRNA
<222> LOCATION: 40; 67
<223> OTHER INFORMATION: Rb 16S rRNA sequence of a new human blood
      bacterium, "n" is unknown

<400> SEQUENCE: 1
cgacgatcag tagctggtct gagaggatga tcagccacan tgggactgag acacggccca      60
gactccnacg ggaggcagca gtggggaata ttggacaatg ggcgcaagcc tgatccagcc     120
atgccgcgtg agtgatgaag gccttagggt tgtaaagctc ttttgtccgg gacgataatg     180
acggtaccgg aagaataagc cccggctaac ttcgtgccaa cagccgcggt aatacgaagg     240
gggctagcgt tgctcggaat cactgggcgt aaagggcgcg taggcggcca tttaagtcgr     300
```

-continued

```
gggtgaaagc ctgtggctca accacagaat tgccttcgat actgggtggc ttgagtccgg      360
aagaggttgg tggaactgcg agtgtagagg tgaaattcgt agatattcgc aagaacaccg      420
gtggcgaagc cggccaactg gtccggaact gacgctgagg cgcgaaagcg tggggagcaa      480
acaggattag ataccctggt agtccacgcc gtaaacgatg aatgccagcc gttgggcagc      540
ttgctgctca gtgcgcagc caacgctttg agcattccgc ctggggagta cggtcgcaag       600
attaaaactc aaaggaattg acgggggcc cgcacaagcg gtggagcatg tggtttaatt       660
cgaagcaacg cgcagaacct taccatccct tgacatggca tgttacccag agagatttgg      720
ggtcctcttc ggaggcgtgc acacaggtgc tgcatggctg tcgtcagctc gtgtcgtgag      780
atgttgggtt aagtcccgca acgagcgcaa cccacgtcct tagttgccat cattcagttg      840
ggcactctag ggagactgcc ggtgataagc cgcgaggaag gtgtggatga cgtcaagtcc      900
tcatggccct tacgggatgg gctacacacg tgctacaatg gcggtgacag agggacgcga      960 agggcgacc tggagcaaat cccgaaaaac cgtctcagtt cggattgcac tctgcaactc      1020
gggtgcatga aggcggaatc gctagtaatc gtggatcagc atgccacggt gaatacgttc      1080
ccgggccttg tacacaccgc ccgtcacacc atgggagttg gtcttacccg acggcgctgc      1140
gccaaccgca aggaggcagg cgaccacggt agggtcagcg actggggtga agtcgtaaca      1200
aggtagcc                                                              1208
```

<210> SEQ ID NO 2
<211> LENGTH: 1502
<212> TYPE: DNA
<213> ORGANISM: unknown
<220> FEATURE:
<223> OTHER INFORMATION: 58 16S rRNA sequence of a new human blood
      bacterium

<400> SEQUENCE: 2

```
gctcggtacc acgcatgctg cagacgcgtt acgtatcgga tccagaattc gtgatgtgtc       60
cagccgcagg ttcccctacg gctaccttgt tacgacttca ccccagtcgc tgaccctacc      120
gtggtcgcct gcctccttgc ggttggcgca gcgccgtcgg gtaagaccaa gtcccatggt      180
gtgacgggcg gtgtgtacaa ggcccgggaa cgtattcacc gtggcatgct gatccacgat      240
tactagcgat tccgccttca tgcactcgag ttgcagagtg caatccgaac tgagacggct      300 tttgggatt tgctccagat cgctccttcg cgtcccactg tcaccgccat tgtagcacgt      360
gtgtagccca tcccgtaagg gccatgagga cttgacgtca tccacacctt cctcgcggct      420
tatcaccggc agtctcccta gagtgcccaa ctgaatgatg gcaactaagg acgtgggttg      480
cgctcgttgc gggacttaac ccaacatctc acgacacgag ctgacgacag ccatgcagca      540
cctgtgtgcg cgccaccgaa gtggacccca atctctctg ggtaacacgc catgtcaaag       600
gatggtaagg ttctgcgcgt tgcttcgaat taaaccacat gctccaccgc ttgtgcgggc      660
ccccgtcaat cctttgagt tttaatcttg cgaccgtact ccccaggcgg aatgctcaaa       720
gcgttagctg cgctactgcg gtgcaagcac cccaacagct ggcattcatc gtttacggcg      780
tggactacca gggtatctaa tcctgtttgc tccccacgct ttcgcgcctc agcgtcagta      840
atggtccagt tggccgcctt cgccaccggt gttcttgcga atatctacga atttcacctc      900
tacactcgca gttccaccaa cctctaccat actcwagcgt cccagtatcg aaggccattc      960
tgtgcttgag ccacaggctt tcaccccga cttaaaacgc gcatacgcg cccttttacg       1020 ccagtgattc cgagcaacgc tagccccctt cgtattaccg cggctgctgg cacgaagtta     1080
```

-continued

```
gccggggcta attcctccgg taccgtcatt atcgtcccgg ataaaagagc tttacaaccc    1140
taaggccttc atcactcacg cggcatggct ggatcaggct tgcgcccatt gtccaatatt    1200
ccccactgct gcctcccgta ggagtctggg ccgtgtctca gtcccagtgt ggctgatcat    1260
cctctcagac cagctactga tcgtcgcctt ggtaggccgt taccccacca actagctaat    1320
cagacgcggg ccgatcttcc ggcagtaaac ctttccccat aagggcgtat ccggtattag    1380
ccctagtttc ccagggttat tccgaaccgg aaggcacgtt cccacgcgtt actcacccgt    1440
ccgccgctga ccccgaaagg tccgctcgac ttgcatgtgt taagcctgcc gccagcgttc    1500
gt                                                                    1502
```

<210> SEQ ID NO 3
<211> LENGTH: 2542
<212> TYPE: DNA
<213> ORGANISM: unknown
<220> FEATURE:
<223> OTHER INFORMATION: Rb 23S rRNA sequence of a new human blood
      bacterium

<400> SEQUENCE: 3

```
gatgggaaa cccaccttcg accctccgta tggtggtctc acgggcgact gtgagattgc      60
catacggttg gtcagatgaa ggtatcaagc cctgaataca ataggggttt gaagcgaacc     120
cggggaactg aaacatctca gtacccggag gaaaggacat caacgagact ccgtcagtag    180
tggcgagcga acgcggatca ggccagtgct tgtgtcgaga ttaccggaac ggtctggaaa    240
ggccggcgcg aagggtgaca gccccgtacg ggacggtcga gacacaagac tcgagtaggg    300
cgggacacgt gaaatcctgt ctgaacatgg ggggaccacc ctccaagcct aagtactcct    360
cagcgaccga tagtgaacca gtaccgtgag ggaaaggtga aaagcacccc gacgagggga    420
gtgaaacagc acctgaaacc ggatgcttac aaacagtggg agcccaaggt tcgtcctggg    480
tgaccgcgta ccttttgtat aatgggtcag cgacttaaag ttacgagcaa gcttaagccg    540
gtaggtggag gcgtagcgaa agcgagtctg aacagggcgt tcagttcgtg gctttagacc    600
cgaaaccgag tgatctagcc atgtgcagga tgaaggtggg gtaacaccca ctggaggtcc    660
gaaccagtgc ccgttgaaaa ggtcttggat gacgtgtggc tagggtgaa aggccaatca    720 aactcggaaa tagctggttc tccgcgaaag ctatttaggt agcgcctcgt gtgaatgcct    780
tgcggggtag agcactggat gggctagggc cgcccacagc ggtaccgcac tcaaccaaac    840
tccgaatacg caagagcact gcacgggaga cacacgcgcg gtgctaacgt ccgtcgtgga    900
gagggaaaca accctgaccg acagctaagg cccccaattc gtggctaagt gggaaaggat    960
gtgggaatcc caaacaacc aggaggttgg cttagaagca gccatccttt aaagaaagcg    1020
taacagctca ctggtctaaa caagggttcc tgcgccgaaa atgtaacggg gctcaagcca    1080
cgagccgaag cttcggtgca tcgcaagatg cgcggtagcg gagcgttccc taggcctgcg    1140
aagggagacc cgtgagggct cctggaggta tgggaagtgc gaatgctgac atgagtaacg    1200
acaaagagtg tgaaagacac tctcgccgaa agtccaaggt tcctgcgta aagttaatct    1260 gcgcagggtt agccggcccc taaggcgagg ccgaaaggcg tagtcgatgg aacggggcg    1320 aatattcccc ggcagtggga tggtgacgga tcccgtgtgt tgttcggcct taacggattg    1380
gtcgggcagc gaaggggtcc caggaaagag cctccacgtg agaccgtacc cgaaaccgac    1440
acaggtggac tggtagagta taccaaggcg cttgagagaa cgatgctgaa ggaactcggc    1500
aatttgcctc cgtaacttcg ggataaggag gcctcgtatg cgggcaaccg tgtgcgaggg    1560
```

-continued

```
gcacagacca gggggtggcg actgtttatc taaaacacag ggctctgcga agtctgtaag      1620
acgacgtata gggcctgacg cctgcccggt gccggaaggt taagaggaga ggtgagagcc      1680
ttgaattgaa gccccggtaa acggcggccg taactataac ggtcctaagg tagcgaaatt      1740
ccttgtcggg taagttccga cctgcacgaa tggcgtaacg atctccccgc tgtctccagc      1800
atcggctcag tgaaattgaa ttccccgtga agatgcgggg ttcctgcggt cagacggaaa      1860
gaccccgtgc acctttactg tagctttgcg ctggccttcg tgtcggcatg tgtaggatag      1920
gtggtaggct ttgaagttcg ggcgccagcc tggatggagc cacccttgaa ataccaccct      1980
tgacgatatg gtggtctaac cgcgcgccct gatcggcgc cgggaccgcg catggcaggc      2040
agtttgactg gggcggtcgc ctcccaaagc gtaacgaagg cgtacgaagg tgggctcaga      2100
gcggtcggaa atcgctcgtc gcgtgcaatg gcataagccc gcttgactgc gagacggaca      2160
tgtcgagcag agacgaaagt cggtcatagt gatccggtgg tcccgcgtgg gtgggccatc      2220
gctcaacgga taaaaggtac gccggggata acaggctgat gaccccaag agtccatatc      2280 gacgggtcg tttggcacct cgatgtcggc tcatcacatc ctgggctgg agaaggtccc      2340 aagggttcgg ctgttcgccg attaaagtgg tacgtgagct gggttcagaa cgtcgtgaga      2400
cagttcggtc cctatctgcc gtgggtgtaa ggagacttga gaggatttgt ccctagtacg      2460
agaggaccgg gatgaacgta cctctggtgg agctgttgtg gcgccagccg cagtgcagcg      2520
tagctacgta cggacgggat aa      2542
```

<210> SEQ ID NO 4
<211> LENGTH: 2061
<212> TYPE: DNA
<213> ORGANISM: unknown
<220> FEATURE:
<223> OTHER INFORMATION: 58 23S rRNA sequence of a new human blood bacterium

<400> SEQUENCE: 4

```
gaaaccaacc ttcgaccttc cgtattgcgg gaccaggcgc gagcctggtt cctcaatacg        60
gttggtcaca tgaaggtatc aaatcctgaa tccatagggg tttgaagcga acccggggaa      120
ctgaaacatc tcagtacccg gaggaaagga catcaacgag actccgtcag tagtggcgag      180
cgaacgcgga tcaggccagt gcctgtgttg agtttaccgg aacggtctgg aaaggccggc      240
gcgatgggtg acagccccgt acgggacgga cgacacacag gactcgagta gggcgggaca      300
cgtgaaatcc tgtctgaaca tgggggggacc acccctccaag cctaagtact cctcagcgac      360
cgatagcgaa ccagtaccgt gagggaaagg tgaaaagcac cccgacgagg ggagtgaaac      420
agcacctgaa accggatgct tacaaacagt gggagcccaa ggttcgtcct gggtgaccgc      480 gtacctttg tataatgggt cagcgactta agttacgag cgagcttaag ccgataggtg      540
gaggcgcagc gaaagcgagt ctgaacaggg cgttcagttc gtggctttag acccgaaacc      600
gagtgatcta gccatgtgca ggatgaaggt ggggtaacac ccactggagg tccgaaccag      660
tgcccgttga aaaggtcttg gatgacgtgt ggctagggt gaaaggccaa tcaaactcgg      720
aaatagctgg ttgtccccga agctatttta ggtagcgcct cgagtgaata cctcacgggg      780
tagagcactg gatgggctag ggccgcccac agcggtacca aacccaacca aactccgaat      840
acgtgagagt actgctcggg agacacacgg cgggtgctaa cgtccgtcgt ggagagggaa      900
acaaccctga ccgacagcta aggcccccaa ttcgtggcta gtgggaaag gatgtgggac      960 tcccaaaaca accaggaggt tggcttagaa gcagccatcc tttaaagaaa gcgtaacagc      1020
```

-continued

```
tcactggtct aaataagggg tcctgcgccg aaaatgtaac ggggctcaag ccacgagccg      1080
aagcttcgga tgcactcctt cggggggtgcg tggtagcgga gcgttccta ggcctgtgaa      1140 gcggtacctg tgaggggccg tggaggtatg ggaagtgcga atgctgacat gagtaacgac      1200
aaagagtgtg aaagacactc tcgccgaaag tccaagggtt cctgcgtaaa gttaatctgc      1260
gcagggttag ccggccccta aggcgaggcc gaaaggcgta gtcgatggga acggggcgaa      1320
cattccccgg ccagcggatg gtgacggatg ccgtgtatcg tttgaccta tcggattggt      1380 caggcggtga aggggtccca ggaaatagcc tccgcgtaag accgtacccg aaaccgacac      1440
aggtggactg gtagagtata ccaaggcgct tgagagaacg atgctgaagg aactcggcaa      1500
tttgcctccg taacttcggg ataaggaggc ctctgtcttg gcaaccagg gcagagggggc      1560 acagaccagg gggtggcgac tgtttatcta aaacacaggg ctctgcgaag tctgtaagac      1620
gacgtatagg gcctgacgcc tgcccggtgc cggaaggtta agaggagagg tgagagcttt      1680
gaatcgaagc cccggtaaac ggcggccgta actataacgg tcctaaggta gcgaaattcc      1740
ttgtcgggta agttccgacc tgcacgaatg gcgtaacgat ctccccgctg tctccagcat      1800
cggctcagtg aaattgaatt ccccgtgaag atgcggggtt cctgcggtca gacggaaaga      1860
ccccgtgcac ctttactgta gctttgcgct ggccttcgtg tcggcatgtg taggataggt      1920
ggtaggcttt gaagcggggg cgtcagcctt cgtggagcca tccttgaaat accacccttg      1980
gcgatatggt ggtctaaccg cgaccccttga tcgggtccg ggaccgcgca tggcaggcag       2040
tttgactggg cgtcgcctcc c                                              2061
```

<210> SEQ ID NO 5
<211> LENGTH: 836
<212> TYPE: DNA
<213> ORGANISM: unknown
<220> FEATURE:
<223> OTHER INFORMATION: intergenic spacer region (IGS) sequence of a new human blood bacterium

<400> SEQUENCE: 5

```
ttctaaggat gttgctggca ggatgatcgg ccggtcttcg gacccggtcc ggtccgctcc        60
tcgtgcgacg tcattggaat atgggctcag tcagagcccc tcatgagcgg gacgctcgtt       120
aagagcggag ccgtcctcgt ttctctttct catccggaca atagcgggat cgccgaggcg       180
gcgtcttcgg acgcctggct ctcggacga ccggctcggg cctgtagctc aggtggttag       240
agcgcacccc tgataagggt gaggtcggac gttcgagtcg tccaggccc accagcttca       300 gtggtcgcaa cgccccgagc cgacggctcg ccgggccgag cggcgcgcgc ggccatctcc       360
gaggaaaacg gggctgtagc tcagttggga gagcggttgc tttgcaagca tcaggtcgtc       420
ggttcgatcc cgtccagctc caccagcgcc ctcgaggctc gcaagaacct cgggcagcgg       480
gtgacgtgag agaagtccgg agagagaggg caagagtttg ccatccgtga gcgcggtgcg       540
cggcgggtcg gcagtgatat cgaacatcgt gaagagggaa tgtggccgtt tggttcttcg       600
aaccatccaa ggtcatgttc ggcaagcatg tgatcgaacc gaaaggttcg gtcactggtc       660
tttatcgtga ccgtggctgg gtgatcggcg acagcgtagc tgctgccgat cgcgccggac       720
atcgatcatg agagcgatca agtgccttaa gagcattcgg tggatgcctt ggcgctgaga       780
ggcgatgaag gacgtggtac gctgcgataa gccttgggga gctgcgaacg agcttt         836
```

<210> SEQ ID NO 6
<211> LENGTH: 592
<212> TYPE: DNA

```
<213> ORGANISM: unknown
<220> FEATURE:
<223> OTHER INFORMATION: a multi drug resistant protein gene of a new
      human blood bacterium

<400> SEQUENCE: 6
acgtatcgga tccagaattc gtgatgtatt cgcgcaacac cgacaaggac ctcgaggtcg      60
cccggcgcat cgaggcgcgg ctgaagcgga ccaagggcct cgtcgacgtg catctccacc    120
agatcgtcga cgtgccgcaa ttcttcgtgg acgtggaccg gcgcctcgcc tccgagctcg    180
gcctgaccca gcagcagatc gcccagagcc tcaacgtctc gctctcgggc tccttccagg    240
tcaccccgaa cttctggacc gacccgaaaa ccggcatccc ctaccagctc tgggtgcaga    300
cacgcaggac atatctgaat tcgtcgacaa gcttctcgag cctaggctag ctctagacca    360
cacgtgtggg ggcccgagct cgcggccgca caattcactg gccgtcgttt tacaacgtcg    420
tgactgggaa aaccctggcg ttacccaact taatcgcctt gcagcacatc ccctttcgc     480 cagctggcgt aatagcgaag aggccgcacc gatcgccctt cccaacagtt gcgcagcctg    540
aatggcgaat ggaaattgta agcgttaata ttttgttaaa attcgcgtta aa            592

<210> SEQ ID NO 7
<211> LENGTH: 31
<212> TYPE: DNA
<213> ORGANISM: artificial sequence
<220> FEATURE:
<221> NAME/KEY: primer_bind
<223> OTHER INFORMATION: primer specific for 16S rRNA of a new human
      blood bacterium

<400> SEQUENCE: 7
gagtttgatc ctggctcaga acgaacgctg g                                    31

<210> SEQ ID NO 8
<211> LENGTH: 31
<212> TYPE: DNA
<213> ORGANISM: artificial sequence
<220> FEATURE:
<221> NAME/KEY: primer_bind
<223> OTHER INFORMATION: primer specific for 16S rRNA of a new human
      blood bacterium

<400> SEQUENCE: 8
catcggcatc cccttggacg ccgacctagt g                                    31

<210> SEQ ID NO 9
<211> LENGTH: 16
<212> TYPE: DNA
<213> ORGANISM: artificial sequence
<220> FEATURE:
<221> NAME/KEY: primer_bind
<223> OTHER INFORMATION: primer specific for 23S rRNA of a new human
      blood bacterium
<300> PUBLICATION INFORMATION:
<301> AUTHORS: Ludwig, et al.
<302> TITLE: Complete 23S ribosomal RNA sequences of gram-positive
      bacteria with a low DNA G+C content
<310> PATENT DOCUMENT NUMBER: System. Appl. Microbiol. 15: 487-501
<311> PATENT FILING DATE: 1992

<400> SEQUENCE: 9
ccgaatgggg vaaccc                                                     16

<210> SEQ ID NO 10
<211> LENGTH: 18
<212> TYPE: DNA
```

```
<213> ORGANISM: artificial sequence
<220> FEATURE:
<221> NAME/KEY: primer_bind
<223> OTHER INFORMATION: primer specific for 23S rRNA of a new human
      blood bacterium
<300> PUBLICATION INFORMATION:
<301> AUTHORS: Ludwig, et al.
<302> TITLE: Complete 23S ribosomal RNA sequences of gram-positive
      bacteria with a low DNA G+C content
<310> PATENT DOCUMENT NUMBER: System. Appl. Microbiol. 15: 487-501
<311> PATENT FILING DATE: 1992

<400> SEQUENCE: 10
tcgaccaaga grrgcttt                                                   18

<210> SEQ ID NO 11
<211> LENGTH: 18
<212> TYPE: DNA
<213> ORGANISM: artificial sequence
<220> FEATURE:
<221> NAME/KEY: primer_bind
<223> OTHER INFORMATION: primer specific for 23S rRNA of a new human
      blood bacterium
<300> PUBLICATION INFORMATION:
<301> AUTHORS: Ludwig, et al.
<302> TITLE: Complete 23S ribosomal RNA sequences of gram-positive
      bacteria with a low DNA G+C content
<310> PATENT DOCUMENT NUMBER: System. Appl. Microbiol. 15: 487-501
<311> PATENT FILING DATE: 1992

<400> SEQUENCE: 11
tagctggttc tcyycgaa                                                   18

<210> SEQ ID NO 12
<211> LENGTH: 19
<212> TYPE: DNA
<213> ORGANISM: artificial sequence
<220> FEATURE:
<221> NAME/KEY: primer_bind
<223> OTHER INFORMATION: primer specific for 23S rRNA of a new human
      blood bacterium
<300> PUBLICATION INFORMATION:
<301> AUTHORS: Ludwig, et al.
<302> TITLE: Complete 23S ribosomal RNA sequences of gram-positive
      bacteria with a low DNA G+C content
<310> PATENT DOCUMENT NUMBER: System. Appl. Microbiol. 15: 487-501
<311> PATENT FILING DATE: 1992

<400> SEQUENCE: 12
ggcattgaag ccctcttcc                                                  19

<210> SEQ ID NO 13
<211> LENGTH: 16
<212> TYPE: DNA
<213> ORGANISM: artificial sequence
<220> FEATURE:
<221> NAME/KEY: primer_bind
<223> OTHER INFORMATION: primer specific for 23S rRNA of a new human
      blood bacterium
<300> PUBLICATION INFORMATION:
<301> AUTHORS: Ludwig, et al.
<302> TITLE: Complete 23S ribosomal RNA sequences of gram-positive
      bacteria with a low DNA G+C content
<310> PATENT DOCUMENT NUMBER: System. Appl. Microbiol. 15: 487-501
<311> PATENT FILING DATE: 1992

<400> SEQUENCE: 13
aaaccgacac aggtrg                                                     16

<210> SEQ ID NO 14
<211> LENGTH: 16
```

```
<212> TYPE: DNA
<213> ORGANISM: artificial sequence
<220> FEATURE:
<221> NAME/KEY: primer_bind
<223> OTHER INFORMATION: primer specific for 23S rRNA of a new human
      blood bacterium
<300> PUBLICATION INFORMATION:
<301> AUTHORS: Ludwig, et al.
<302> TITLE: Complete 23S ribosomal RNA sequences of gram-positive
      bacteria with a low DNA G+C content
<310> PATENT DOCUMENT NUMBER: System. Appl. Microbiol. 15: 487-501
<311> PATENT FILING DATE: 1992

<400> SEQUENCE: 14
cgacttycgt agattc                                                16

<210> SEQ ID NO 15
<211> LENGTH: 17
<212> TYPE: DNA
<213> ORGANISM: artificial sequence
<220> FEATURE:
<221> NAME/KEY: primer_bind
<223> OTHER INFORMATION: primer specific for intergenic spacer region
      (IGS) sequence of a new human blood bacterium

<400> SEQUENCE: 15
acggtagggt cagcgac                                               17

<210> SEQ ID NO 16
<211> LENGTH: 17
<212> TYPE: DNA
<213> ORGANISM: artificial sequence
<220> FEATURE:
<221> NAME/KEY: primer_bind
<223> OTHER INFORMATION: primer specific for intergenic spacer region
      (IGS) sequence of a new human blood bacterium

<400> SEQUENCE: 16
cctcccagct tccaccc                                               17

<210> SEQ ID NO 17
<211> LENGTH: 18
<212> TYPE: DNA
<213> ORGANISM: artificial sequence
<220> FEATURE:
<221> NAME/KEY: primer_bind
<223> OTHER INFORMATION: primer specific for a multi drug resistant
      protein gene of a new human blood bacterium

<400> SEQUENCE: 17
atgtcctgcg tgtctgca                                              18

<210> SEQ ID NO 18
<211> LENGTH: 18
<212> TYPE: DNA
<213> ORGANISM: artificial sequence
<220> FEATURE:
<221> NAME/KEY: primer_bind
<223> OTHER INFORMATION: primer specific for a multi drug resistant
      protein gene of a new human blood bacterium

<400> SEQUENCE: 18
gtactagtcc agcgtgtc                                              18

<210> SEQ ID NO 19
<211> LENGTH: 16
<212> TYPE: DNA
<213> ORGANISM: artificial sequence
<220> FEATURE:
```

```
<221> NAME/KEY: primer_bind
<223> OTHER INFORMATION: probe for in situ hybridization

<400> SEQUENCE: 19
tcgcagttcc accaac                                                          16

<210> SEQ ID NO 20
<211> LENGTH: 16
<212> TYPE: DNA
<213> ORGANISM: artificial sequence
<220> FEATURE:
<221> NAME/KEY: primer_bind
<223> OTHER INFORMATION: probe for in situ hybridization

<400> SEQUENCE: 20
ctgtggttga gccaca                                                          16
```

HUMAN BLOOD BACTERIUM

CROSS-REFERENCE TO RELATED APPLICATIONS

This patent application claims benefit of provisional patent application U.S. Serial No. 60/064,472, filed Nov. 6, 1997, now abandoned.

BACKGROUND OF THE INVENTION

Field of the Invention

The present invention relates generally to bacteriology and human pathology. More specifically, the present invention relates to a bacterium present in the human blood, the characterization, culturing and diagnostic methodologies therefor and the treatment of pathophysiological states caused by this bacterium.

Description of the Related Art

Infectious agents are a main cause of human disease and the leading cause of death worldwide. Bacterial infections are cause more deaths than any other class of infectious organisms. The single leading cause of death via infectious organisms worldwide remains tuberculosis, caused by the bacterium Mycobacterium tuberculosis; however scores of diseases or disorders caused by infectious agents are present in both developed and undeveloped countries.

Examples of infectious disorders include chronic fatigue syndrome and conditions such as fibromyalgia. These disorders affect about 1,000,000 Americans. There is no known cause or effective treatment for these conditions, nor is there any definitive diagnostic laboratory test. Epidemiologic evidence suggests an infectious agent as the cause; however, no causative infectious agent has been identified.

Multiple sclerosis produces disability to variable degrees and occasional death in about 400,000 Americans. Multiple sclerosis is a disease of unknown cause and has considerable variability, with minimal disability in some patients and almost total disability in others. As with chronic fatigue syndrome, there is no definitive diagnostic laboratory test, and clinical diagnosis is based on a constellation of symptoms and tests. Epidemiologic data suggests that multiple sclerosis has an underlying infectious cause and that the infectious cause is acquired years prior to the development of symptoms.

Another loosely-defined group of diseases are those in the "autoimmune" category such as lupus erythematosis and rheumatoid arthritis. These relatively common diseases are often disabling and the underlying cause of these diseases is unknown. Rheumatoid arthritis is rarely fatal, but lupus erythematosis has a significant mortality rate. Laboratory diagnostic tests for these conditions are satisfactory, but no test is definitive, so a variety of tests in combination with the correlation of clinical symptoms is necessary. A variety of medications are available to control symptoms to some degree and slow progression of the diseases, but no treatment is curative. Certain antibiotics are currently accepted as one therapeutic option for rheumatoid arthritis, but no specific infectious cause has been demonstrated.

Thus, the prior art is deficient in the identification and characterization of the specific bacterium from human blood described herein, methods for culturing it and for diagnosing and treating diseases that result from an increase in the presence of the bacterium in an individual's blood. The present invention fulfills this long-standing need and desire in the art.

SUMMARY OF THE INVENTION

One object of the present invention is to provide a culture system for the human blood bacterium (HBB) described herein. One approach to this culture system is to provide a method for culturing HBB, comprising the steps of: isolating HBB from a sample; adding a medium comprising salts, at least one sugar, and lactalbumin hydrolysate; and incubating said HBB at a temperature which allows for growth of said HBB.

In one embodiment of the present invention, there is provided a method for culturing HBB, comprising the steps of: isolating HBB from a sample; adding a medium comprising $CaCl_2$; $MgCl_2$ (anhydrous); KCl; NaCl; $NaH_2PO_4$ (monobasic); lactalbumin hydrolysate; yeast extract, lactose; manganese chloride; and a buffer selected from the group of sodium bicarbonate, Tris, and HEPES; and incubating said HBB at a temperature which allows for growth of said HBB. In a preferred embodiment, the culture medium further contains sodium arachidonate and lipoxidase.

In yet another embodiment of the present invention, there is provided a method for culturing HBB, comprising the steps of: isolating HBB from a sample; adding a medium comprising $CaCl_2$; $MgCl_2$ (anhydrous); KCl; NaCl; $NaH_2PO_4$ (monobasic); lactalbumin hydrolysate; yeast extract; manganese chloride; and a sugar selected from the group of glucose, fructose, and sucrose; and incubating said HBB at a temperature which allows for growth of said HBB.

An additional object of the present invention is to provide methods of diagnosing a pathophysiological state in an individual that results from an increase in the presence of the human blood bacterium (HBB) in an individual's blood. Additionally, the methods can be used to identify individuals at risk for developing a pathophysiological state or for monitoring progress of treatment for disease. The methods make use of antibodies capable of reacting with HBB and polynucleotides capable of duplexing with the HBB genome. Infection may be detected by various techniques, particularly nucleic acid hybridization and immunoassays.

In another embodiment of the present invention, there is provided a method for diagnosing a pathophysiological state in an individual resulting from an imbalance in a presence of HBB in the individual's blood, comprising the step of determining a count of HBB from blood of the individual, and comparing the counts between the test and control individuals, wherein the control individual is known to be healthy. If the count of test individual is greater than that of control individual, the test individual has abnormal levels of HBB in its blood. Otherwise, the test individual has normal levels of HBB. Preferably, the count from control individual is no greater than 400/HPF (High power field) after growing its blood for 1 week in medium O or modified RPMI medium. The methods for making this determination include, but are not limited to, a technique selected from the group of quantification by a solid or liquid culture; ELISA assay; flow cytometry; TAQ man; Western blot hybridization; antibody-based tests and nucleic acid-probe based tests including PCR and in situ hybridization. Specifically, probes for in situ hybridization are selected from the group consisting of SEQ ID No: 19 and SEQ ID No:20. Primers used for PCR are selected from the group consisting of SEQ ID Nos: 7–18.

A further object of the present invention is to treat a pathophysiological state that results from an increase in the presence of the bacterium in an individual's blood. In one embodiment of the present invention, there is provided a method for treating a pathophysiological state that results from an imbalance in a presence of HBB in an individual's blood, comprising the step of administering to said individual a therapeutically effective amount of at least one antibiotic from the group consisting of penicillin G, penicillin V, primaquine, Augmentin, dicloxacillin, Ciprofloxacin, Isoniazid, third-generation cephalosporins, azithromycin, clarithromycin, chloroquin, hydroxychloroquin, minocycline, doxycycline. In a preferred embodiment, the antibiotic is administered with a therapeutically effective amount of one or more substances from the group consisting of probecid, Nystatin, Nizoral, Diflucan, steroids, vitamin B-6, vitamin C, folic acid, vitamin E, niacin, chromium, zinc, sulfhydryl compounds, steroids, and ibuprofen.

In yet another embodiment of the present invention, there is provided a vaccine generated from HBB or components thereof.

In still yet another embodiment of the present invention, there is provided a method of treating an individual with a disease where toxic metabolites are accumulated in its plasma or serum by administering engineered HBB to the individual. Preferably, the engineered HBB expresses therapeutical gene products selected from the group consisting of hormones, growth regulators, antitumor antigens, antibodies, interleukins and other therapeutical antigens.

Still another project of the present invention is to characterize this new human blood bacterium.

In one embodiment of the present invention, there is provided human blood bacterium in a normal individual's blood having a 16S rRNA sequence shown in SEQ ID No: 1.

In another embodiment of the present invention, there is provided human blood bacterium in a diseased individual's blood having a 16S rRNA sequence shown in SEQ ID No: 2. Preferably, the individual has a disease selected from the group consisting of chronic fatigue syndrome, multiple sclerosis, lupus erythematosis, rheumatoid arthritis and fibromyalgia.

In still another embodiment of the present invention, there is provided human blood bacterium in a normal individual's blood having a 23S rRNA sequence shown in SEQ ID No: 3.

In still yet another embodiment of the present invention, there is human blood bacterium in a diseased individual's blood having a 23S rRNA sequence shown in SEQ ID No: 4. Preferably, the individual has a disease selected from the group consisting of chronic fatigue syndrome, multiple sclerosis, lupus erythematosis, rheumatoid arthritis and fibromyalgia.

In yet another embodiment of the present invention, there is provided human blood bacterium having an intergenic spacer region sequence shown in SEQ ID No: 5. Preferably, primers specific for the intergenic spacer region having a sequence shown in SEQ ID No:15 or SEQ ID No:16.

In still yet another embodiment of the present invention, there is provided human blood bacterium having a drug resistant protein gene sequence shown in SEQ ID No: 6.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
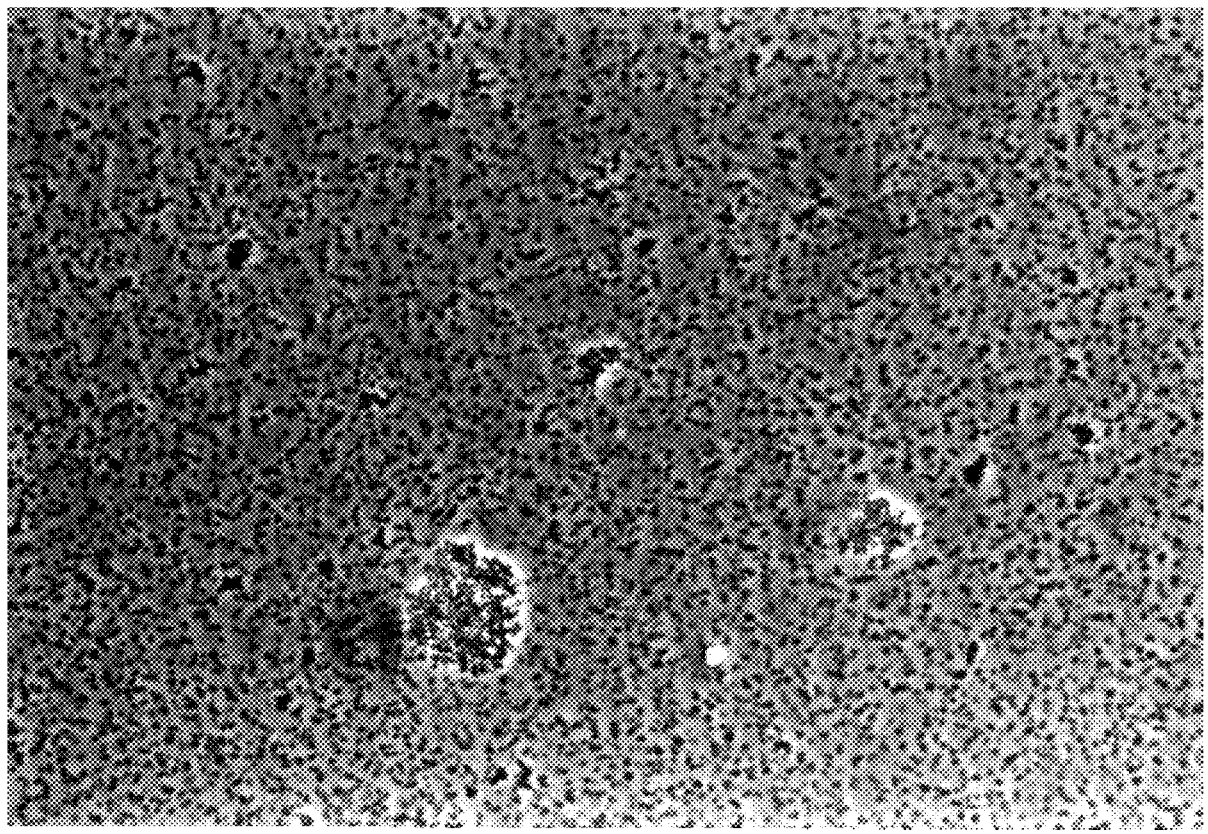
FIG. 1 shows a culture from serum in medium L after one week's growth. A relatively large number of bacteria is present, ranging in appearance from cocci to short bacilli. Most are isolated, but some clumps of organisms are noted. Magnification approx. 600x, phase contrast.
Figure 2:
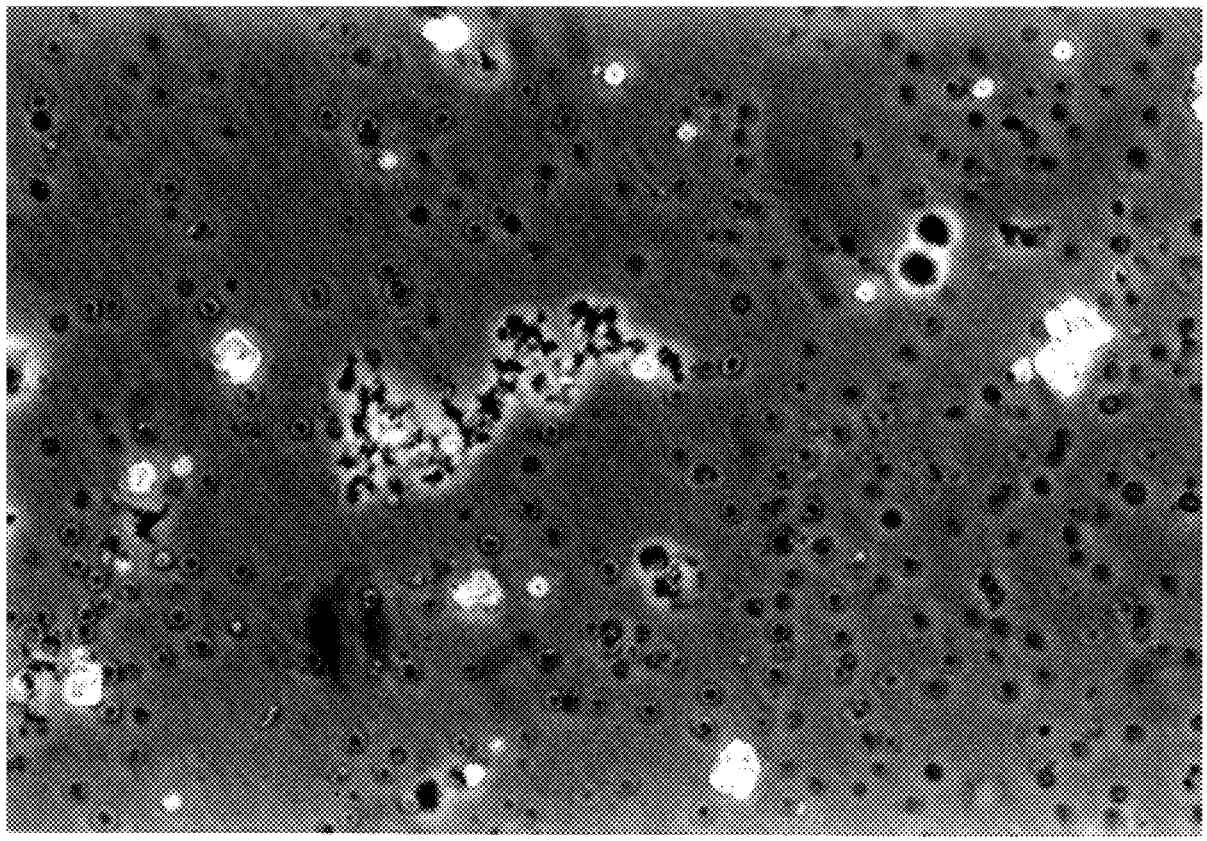
FIG. 2 is a photomicrograph of a culture from serum in medium L. In contrast to FIG. 1, a much lower concentration of bacteria is present. In this culture, atypical forms dominate, with marked variation in size and refractility. Many are round and many show budding-like division. Most are phase-dark, but some contain phase-bright inclusions and crystal-like phase-bright bodies are also present. The background contains many red blood cell ghosts which are uniform in size and low in contrast; the majority are out of focus. Magnification approx. 600x, phase contrast.

As used herein, the term "human blood bacterium" or "HBB" refers to a bacterium described herein that is present in the blood of essentially all humans which can be grown in the culture system described herein. Elevated levels of HBB indicate the presence of or likelihood of developing certain diseases such a s chronic fatigue syndrome, multiple sclerosis and other autoimmune diseases. Further, there is a 100% correlation between a decrease in the presence of HBB in the blood and a diminishing or complete elimination of symptoms of these diseases.

As used herein, the term "antibiotic" refers to a chemical or drug which inhibits selectively the growth of a bacterium or kills it completely.

As used herein, the term "autoimmune disease" refers to a disease characterized by an immune reaction created by the host that is directed against specific components of the host's body.

As used herein, the term "bacterial growth" refers to an increase in the number of bacteria as a result of division of a bacterium into two or more progeny.

As used herein, the term "bacterial culture" refers to a collection of bacteria growing in or on a nutritive mixture of materials in vitro.

As used herein, the term "exudate" or "slime" refers to a complex material produced by bacteria that is semi-solid in consistency.

As used herein, the term "improved" in the context of disease treatment refers to a decrease in the severity of reported symptoms or in other objective signs which characterize a particular disease.

The present invention is directed to methods of culturing a human blood bacterium (HBB) useful in diagnosing pathophysiological states in individuals that result from an increase in the presence of this bacterium in an individual's blood. It is contemplated additionally that the methods of the present invention can be used to identify individuals at risk for developing such a pathophysiological state or for monitoring progress of treatment. Further, the methods of the present invention, drawn to controlling the human blood bacteria by antibiotics or through genetic engineering, may be used treat a pathophysiological state that results from an increase in the presence of the bacterium in an individual's blood.

In accordance with the present invention there may be employed conventional molecular biology, microbiology, and recombinant DNA techniques within the skill of the art. Such techniques are explained fully in the literature. See, e.g., "Current Protocols in Molecular Biology", Volumes 1–3 (Ausubel et al., Ed, 1994–1997, John Wiley and Sons); Sambrook, Fritsch & Maniatis, "Molecular Cloning: A Laboratory Manual (1989); "DNA Cloning: A Practical Approach," Volumes I and II (D. N. Glover ed. 1985); "Oligonucleotide Synthesis"(M. J. Gait ed. 1984); "Nucleic Acid Hybridization"(B. D. Hames & S. J. Higgins eds. (1985)); "Transcription and Translation"(B. D. Hames & S. J. Higgins eds. (1984)); "Animal Cell Culture"(R. I. Freshney, ed. (1986)); "Immobilized Cells And Enzymes" (IRL Press, (1986)) and "Current Protocols in Immunology", Volumes 1–3 (Ausubel et al., Ed, 1994–1997, John Wiley and Sons).

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein, only the sequence in the 5' to 3' direction along the nontranscribed strand of DNA is given (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The term "oligonucleotide" or "probe" as used herein, refers to a molecule comprised of ribonucleotides or deoxyribonucleotides. The exact size of the oligonucleotide or probe will depend upon many factors which, in turn, depend upon the ultimate function and use of the oligonucleotide. Diagnostic tests for detecting the presence of HBB in biological samples may be performed using polynucleotide probes. Such polynucleotide probes may be prepared based on the sequence of the HBB genome. The length of the probe is not critical, but will usually comprise at least about 12 bases, more usually comprising at least about 16 bases, such that the probe is substantially complementary to a portion of the bacterial genome; however, the probe need not have perfect complementarity with the HBB genome. The probes may be prepared synthetically, with suitable synthetic techniques, and most likely include a detectable label. Usually, the synthetic sequences are expanded in common, publicly-available cloning vectors and suitable hosts in order to obtain large quantities of the probe. The expanded vectors may themselves be labeled for use as probes, or shorter fragments containing complementary strands may be excised and labeled. Methods for the preparation and utilization of nucleotide probes for diagnostic testing are described in the references listed above, supra, and in U.S. Pat. No. 4,358,535 to Falkow, et al.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

Polypeptides used for detection and diagnosis of methods of the present invention are either haptenic or antigenic, include at least six amino acids, and include usually at least twelve or more amino acids found contiguously within one of the natural HBB proteins. Polypeptides generally correspond to at least one epitopic site which is characteristic of HBB, preferably to epitopes associated with B and/or T cells. The term "characteristic" in this context means that the epitopic site allows immunologic detection of HBB in a physiological sample with reasonable assurance. Usually, it is desirable that the epitopic site be immunologically distinct from bacteria other than HBB. The HBB polypeptides may be natural; i.e., including an entire HBB protein or fragments thereof isolated from a natural source, or the polypeptides may be synthetic. Natural polypeptides may be isolated and used to prepare an affinity column by techniques known in the art. Such techniques are taught, for example, in Hudson and Hay, Chapter 8, Practical Immunology, Blackwell Scientific Publications, Oxford (1980).

Synthetic polypeptides which are immunologically cross-reactive with a natural HBB protein may be produced by two general methods. First, polypeptides having fewer than about 80 amino acids may be synthesized by the Merrifield solid-phase synthesis method where amino acids are sequentially added to a growing chain. An alternative method involves expression in cultured cells of recombinant DNA molecules encoding a desired portion of the HBB genome. The portion of the HBB genome may itself be natural or synthetic, with natural genes obtainable from the isolated bacterium by conventional techniques.

To be useful in the detection and diagnostic methods of the present invention, the polypeptides are obtained in a substantially pure form. The proteins may be purified by use of the antibodies described hereinafter using immunoabsorbant affinity columns. Once a sufficient quantity of HBB polypeptides has been obtained, polyclonal antibodies specific for HBB may be produced by in vitro or in vivo techniques. In vitro techniques involve in vitro exposure of lymphocytes to the antigenic polypeptides, while in vivo techniques require the injection of the polypeptides into a wide variety of vertebrates. Suitable vertebrates are non-human, and include mice, rats, rabbits, sheep, goats, donkeys and the like. Polypeptides having more than about thirty amino acids, usually more than about fifty amino acids, may serve directly as the immunogen. If the polypeptide is smaller than about 10kD, particularly less then about 6kD, it may be necessary to join the polypeptide to a larger molecule to elicit the desired immune response. The immunogens are then injected into the animal, and the animal is bled periodically with successive bleeds having improved titer and specificity. Injections may be made intramuscularly, subcutaneously, and an adjuvant, such as incomplete Freund's adjuvant, will usually be employed.

If desired, monoclonal antibodies can be obtained by preparing immortalized cell lines capable of producing antibodies having the desired specificity. Such immortalized cell lines may be produced in a variety of ways. Conveniently, a small vertebrate, such as a mouse, is hyperimmunized with the desired antigen by the method just described. The vertebrate is then killed, usually several days after the final immunization, the spleen removed, and the spleen cells immortalized. Presently, the most common technique is fusion with a myeloma cell fusion partner, as first described by Kohler and Milstein, Eur. J. Immunol., 6:511-19 (1976). Other techniques include EBV transformation, transformation with oncogenes, and transformation with retroviruses, or any other method which provides for stable maintenance of the cell line and production of monoclonal antibodies.

When employing fusion with a fusion partner, the manner of fusion is not critical and various techniques may be employed. Commonly, the spleen and myeloma cells are combined in the presence of a non-ionic detergent, usually polyethylene glycol, and other additives such as Dulbecco's Modified Eagle's medium for a few minutes. At the end of the fusion, the non-ionic detergent is removed by washing the cells. The fused cells are promptly dispensed in small culture wells (usually in a microtiter plate at relatively low density, at about $5\times10^6$ cells/well) in a selective medium chosen to support growth of the hybrid cells while being lethal to the myeloma cells. Usually, the myeloma cell line has been mutated to be sensitive, and the medium includes a HAT concentration sufficient to inhibit the proliferation of the unfused myeloma cells. After sufficient time, usually from about one to two weeks, colonies of hybrids are observed and plates containing hyperpositive wells are identified. The plates and wells having only one colony per well are selected, and supernatants from these wells are tested for binding activity against HBB or a particular HBB protein. Once positive hybridomas are identified, the cell line can be maintained as a viable culture.

Further screening of the hybridomas may be desirable, depending on the desired use for the antibodies. For use i n immunodiagnostic assays, antibodies having very high specificity and affinity for the antigenic site of an HBB polypeptide of this invention are desirable. Thus, once the desired hybridomas have been selected, monoclonal antibodies may be isolated from supernatants of the growing colonies. The yield of antibodies obtained, however, is usually low, but may be enhanced by various techniques such as injection of the hybridoma cell line into the peritoneal cavity of a vertebrate host. Most antibodies may then be harvested from the ascites fluid or from the blood. Proteins and other contaminants are removed from the monoclonal antibodies prior to use by conventional techniques; e.g., chromatography, gel filtration, precipitation or extraction. Alternatively cDNAs encoding the antibody chains can be obtained by known methods and host cells can be transformed with vectors containing the cDNA to produce the anti-HBB antibodies recombinantly.

Polypeptides and antibodies of the present invention may be used with or without modification for the detection of HBB. Frequently, the polypeptides and antibodies are labeled by either covalently or non-covalently combining the polypeptide with a second substance which provides for detectable signal. A wide variety of labels and conjugation techniques are known and are reported extensively in both the scientific and patent literature. Some of the labels include radionuclides, enzymes, substrates, cofactors, inhibitors, fluorescers, chemiluminescers, magnetic particles and the like.

Antibodies and polypeptides prepared as described above can be used in various immunological techniques for detecting HBB and anti-HBB antibodies in physiological specimens, particularly body fluid samples including blood, blood serum, and cerebrospinal fluid. Depending on the nature of the sample, both immunoassays and immunohistochemical staining techniques may be used. Liquid phase immunoassays and Western blot analysis are used in detection of HBB in blood and CFS. The use of antibodies in protein binding assays is well established. Numerous competitive and noncompetitive protein binding assays have been described in the scientific and patent literature, and a large number of such assays are commercially available. Detailed methods for detecting the presence of HBB from blood or CFS is set out in the Experimental Section. Additionally, a general protocol for enzyme linked immunosorbent assays (ELISAs) for detecting presence of antibodies to HBB in blood are also set forth in Example 9.

It is specifically contemplated that pharmaceutical compositions may be prepared using the novel engineered HBB of the present invention. In such a case, the pharmaceutical composition comprises the novel engineered HBB and a pharmaceutically acceptable carrier. In addition, it is contemplated that various antibiotics known to the art may be used to treat the autoimmune conditions and other diseases associated with HBB. A person having ordinary skill in the art of molecular pharmacology would be able to determine readily, without undue experimentation, the appropriate dosages and routes of administration of either the HBB of the current invention, or the antibiotics used in the methods of treatment of disease of the present invention. When used in vivo for therapy, the engineered HBB or the antibiotic is administered to the patient or to an animal in therapeutically effective amounts; i.e., amounts that reduce or eliminate the bacteria in the bloodstream in the case of treatment of autoimmune disease. The dose and dosage regimen will depend upon the nature of the disease, the stage of infection, the characteristics of the particular pharmacologic agent— e.g., its therapeutic index, the patient, the patient's history and other factors. The schedule will be continued to optimize effectiveness, balanced against negative effects of treatment. See Remington's Pharmaceutical Science, 17th Ed. (1990) Mark Publishing Co., Easton, Pa.; and Goodman and Gilman's: The Pharmacological Basis of Therapeutics 8th Ed (1990) Pergamon Press.

Antibiotic treatment generally will not be via parenteral administration due to the very slow growth cycle of HBB and probable existence of spores or a spore-like state. The existence of a spore-like state requires that any antibiotic therapy be carried out over a long time span, compared to more typical antibiotic therapy. Parenteral administration over a long period of time is inconvenient; intravenous administration in particular over a long time carries serious risks of infection, embolism, and other complications.

The engineered HBB of the present invention may be administered parenterally. For parenteral administration, the engineered HBB will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives.

The present invention reports a newly-identified and characterized human blood bacterium (HBB). The bacterium is present in the bloodstream of all humans in very low numbers—too low to recognize when examining blood smears—although it has been seen on direct observation of blood. There have been sporadic observations over the years that may have been HBB, but HBB has never been successfully cultured or characterized in the prior art. The bacterium appears to be associated with several diseases, either directly or indirectly. It is almost certainly the underlying (indirect) cause of the chronic fatigue syndrome. Further, it is also associated with multiple sclerosis. Further observations indicate that it is related to other "autoimmune" diseases.

One of the most notable features of HBB is its very slow and limited growth. Levels of $10^6$ to $10^8$ bacteria per culture flask can be recovered from 1 ml of serum after one week's growth. The number of organisms in blood samples prior to culture is still not known precisely, but is at least one to two orders of magnitude lower. The slow growth restricts characterization and requires running experiments for longer time than is usual for bacteriologic studies, typically from days up to a month.

Blood culture is done normally by inoculating whole anticoagulated blood into a complex medium that provides a variety of nutrients for bacterial growth. Different media and culture conditions are typically required to grow different bacteria; nevertheless most bacteria that are cultured from the blood have a rapid growth rate and grow essentially without limit as long as nutrients are supplied, so very high numbers are eventually achieved. It is routine to culture blood specimens for no more than one week. However, HBB cannot be cultured in this way because growth is slow and the ultimate level of growth is limited—sufficient growth is not achieved to identify the bacteria in the presence of large numbers of red blood cells. In addition, most ordinary culture media does not supply the necessary nutrients for HBB and contains materials that actively inhibit growth. Further, the observation that HBB could be recovered from serum is counterintuitive, as organisms are generally trapped in the clot. The actual composition of the culture medium used in the experiments leading to the present invention was developed from a long series of trial and error experiments extending over several years, typically running each experiment over a month or more. The single most important component of the medium, the lactalbumin hydrolysate, is occasionally used as a bacterial culture medium component, but is relatively unusual.

The techniques utilized in the present invention and described herein were run using standard bacteriologic techniques, but with the periods of time for culture and chemical analysis extended. Where the experiments compare growth, controls without additives were run parallel to the experimental cultures. For biochemical tests, uninoculated medium was used as a control.

The following examples are given for the purpose of illustrating various embodiments of the invention and are not meant to limit the present invention in any fashion.

EXAMPLE 1

Characterization

HBB has only been recovered from "sterile" human sources, i.e., human blood and cerebrospinal fluid (CSF). Because of the very slow growth of HBB, other organisms would be expected to overgrow HBB rapidly in cultures from nonsterile sources. To culture HBB from blood, the blood was allowed to clot, retract and draw off the serum containing HBB. A remarkable feature of the bacterium is that it does not get trapped in the clot. The easiest and most reproducible approach to isolate HBB is to use a sterile vacutainer-type clot tube with a separator gel. The serum was then centrifuged so as to obtain the bacteria, or the serum was aspirated in a sterile manner for culture. Alternatively, blood can be drawn in a vacutainer-type clot tube without a separator gel and allowed to clot and retract, and prior to culturing, the tube is inverted to resuspend organisms. The red cells are allowed to settle, and the cell-free serum above th e cell layer is aspirated for culture.

Cerebrospinal fluid can be cultured via lumbar puncture in a sealed sterile tube.

HBB can be isolated from the bloodstream of any individual, although the degree of infection varies considerably. It has been recovered from at least 21 normal subjects, over 75 subjects with "chronic fatigue syndrome" and over 100 subjects with multiple sclerosis. There is some overlap between the levels of bacteria in the normal population and those with the chronic fatigue syndrome and multiple sclerosis, but there is a correlation between elevated levels of the bacterium and the presence of active symptoms of these diseases. It has been recovered from the cerebrospinal fluid of multiple sclerosis patients.

The fact that HBB is always present in the bloodstream implies first that the body lacks effective defense against it, and second, that something critical to its growth is available in a restricted amount, thus preventing its overgrowth.

EXAMPLE 2

Culture Method

Routine culture was done in broth cultures in T-25 cell culture flasks using either medium L or medium O, or 1/2 strength medium O or RPMI-1640 cell culture medium with or without modification. Normally 1 ml of serum was added to 9 ml of medium. Larger flasks with a proportionately larger amount of serum and medium are used to produce bacteria in quantity. Modulators might be added to some flasks in 10x or higher concentration (corresponding to addition of 1 ml or less). When examining the effect of modulators, control flasks were prepared similarly without the addition of the modulator. Levels were observed microscopically (inverted phase microscope, observing the number of organisms per field crudely or by actual count) after incubation, typically at several points in time.

When multiple comparisons were done at once, they were done in 12 well or 24 well cell culture plates, most often the latter. With the latter, typically 1 ml of medium inoculated with serum is added to each well, with modulators added at 10X or higher concentration (0.1 ml or less). When comparisons are done in well plates, control wells without any additions are included. Levels were observed microscopically (inverted phase microscope) after incubation, typically at several points in time. The well plate cultures were also used for antibiotic sensitivity testing.

Solid medium with agarose added to the formulations has been used for specific studies, but it is generally less satisfactory. The bacteria penetrate 1.5% agarose; at 2% and above they will remain on the surface, but colonies are not formed due to their movement over the surface. This type of medium has only been used for attempts to determine antibiotic sensitivity by Kirby-Bauer technique. Ordinary bacteriologic agar, as opposed to agarose, strongly inhibits growth, partly explaining the failure to isolate the bacterium with conventional media.

EXAMPLE 3

Culture Conditions

The bacterium is strictly aerobic, and requires no $CO_2$. HBB is temperature tolerant with an optimum growth around 33–37° C., but survives for long periods of time refrigerated, and can withstand temperatures up to 50° C. in culture; however, both high and low temperatures retard growth of HBB (1). HBB can b e recovered successfully from serum in vacutainer clot tubes that have been refrigerated for several weeks. Typically there is good growth of HBB in culture for a few weeks, then growth slows and eventually stops, often with degeneration. Subculture of HBB stimulates further growth; however this process ceases after a few subcultures. The growth rate of HBB is very slow in comparison to most bacteria, with a doubling time typically ranging from a few days to over a week. HBB can remain viable in a sealed culture flasks for up to about a year, although if the culture system is modified to stimulate growth, degeneration is more likely to develop.

HBB apparently can enter a metabolically inactive state which is likely a true spore state. The yield of organisms from the blood varies with the individual and the individual's health, but typically 1 ml of serum yields $10^6$ to $10^8$ organisms after a week's growth using medium O or L; corresponding to about 25→1000 bacteria per high power field in a Corning T-25™ flask using approximately 9 ml of medium.

Serum from several patients was submitted to a local bacterial reference laboratory, where no growth was obtained either aerobic or anaerobic on the various media typically used to grow bacterial strains from patient samples, although same serum grew well in above described culture media.

EXAMPLE 4

Growth Requirements and Modulators

Bacterial growth requires lactalbumin hydrolysate and yeast extract. Division of the bacterium is inhibited slightly by brain-heart infusion, which produces longer bacilli. A sugar is apparently required, and it has been determined that the following sugars support growth: glucose, sucrose, fructose, lactose, dextran, raffinose and meilibose. A combination of glucose, sucrose, and fructose and/or of lactose and glucose has permitted isolation of HBB in 100% of subjects tested (>300 isolations). The addition of pyruvate to growth media produces longer bacilli with increased motility and increases the amount of slime produced by the bacteria. In contrast, pyruvate stimulates growth in 1/2-strength medium O or RPMI-1640 when exposed to a grow-light and especially when in flasks with gas-permeable caps. There are no known vitamin requirements other than those supplied by yeast extract. There appears to be no inhibition by methotrexate in the isolates tested.

Simple salts are required for growth and growth is stimulated by several trace metal ions, including manganese (1 $\mu$g/ml optimum), copper, tin, iron, mercury, and silver. Growth appears to be inhibited by zinc, but is or may be stimulated by stannous tartrate (14 $\mu$g/ml), tin ethyl hexanoate (14 $\mu$g/ml), tin caproate (<14 $\mu$g/ml), or dibutyltindilaurate (1.4 $\mu$g/ml). Growth might also be stimulated by hydrogen peroxide and (oxidized) arachidonate (2–10 $\mu$g/ml).

There appears to be a slight stimulation with titanium ethoxide (1/14 saturated), benzophenone (1/14 saturated), diphenylamine (1/14 saturated), tetraethylmethylenediamine (14 $\mu$g/ml), morpholine (1.4 $\mu$g/ml) and ubiquinone ($Q_{10}$) (1/5 saturated). Little or no stimulation or inhibition was observed by chromium picolinate, silver proteinate, amantadine, potassium iodide, picolinic acid, borax (14 $\mu$g/ml), dichlorophenylenediamine (1/14 saturated), spermine (7–10 $\mu$g/ml), zirconium chloride (1.4 $\mu$g/ml), titanium butoxide (1/14 saturated), resazurin (14 $\mu$g/ml), methylene blue (14 $\mu$g/ml), fluorescein (14 $\mu$g/ml), L-carnitine (2 $\mu$g/ml), phosphorylethanolamine (3 $\mu$g/ml), orotic acid (4 $\mu$g/ml), cysteine (20 $\mu$g/ml), sodium sulfide (20 $\mu$g/ml), N-acetyl cysteine (20 $\mu$g/ml), ammonium sulfate (20 mg/ml), 2-mercaptoethanol (10 $\mu$g/ml), dithiotheitol (10 $\mu$g/ml), taurine 20 $\mu$g/ml). No effect of light level (1) was observed when using medium L or medium O and ordinary sunlight or fluorescent light, but stimulation of growth is observed with grow-lights or special blue incandescent lights or special bluish fluorescent lights, particularly with 1/2 strength O or RPMI-1640. The effect is enhanced when flasks with gas-permeable caps are used. One isolate tested grew very slowly on a Sabouraud's dextrose medium (Difco) slant over six month's time at room temperature. No anaerobical growth was observed in Difco Anaerobic Culture System, while more than 300 isolates grew well without $CO_2$.

HBB has been found to be moderately pH tolerant, growing over a tested range of 5.8–9.0, with the optimum pH varying with the strain. There is no significant effect of sodium sulfide (20 µg/ml), n-acetyl cysteine, mercaptoethanol, or dithiothreitol. Cysteine (20 µg/ml) appears to inhibit growth in some isolates, methionine (20 µg/ml) appears to do so less consistently. There is no effect of ammonium sulfate or taurine on the growth. Some stimulation of growth was observed when alcohols were added (3.3% ethanol, 3.3% n-butanol, 1.67% isoamyl alcohol). Additionally, there was no effect on reduction of cell wall-defective forms from addition of cell wall precursors N-acetylglucosamine, N-acetyllactoasamine, muramic acid, N-acetylmuramic acid, diaminopimelic acid, although some stimulation of culture growth was observed with several of these, particularly N-acetylactosamine. Oxidative inhibitors had little effect on growth, such as azide, cyanide and dinitrophenol.

EXAMPLE 5
Culture Medium

Dozens of formulae have been tested and several formulae have been used, based on the medium used for the initial, successful isolation and subsequent experiments. The following formula—referred to as medium L—has been developed and found to give much better performance: IL of Mitsuhashi-Maramorosch insect cell culture medium (Sigma) or its components minus the glucose; namely, $CaCl_2$: 0.15102 g; $MgCl_2$ (anhydrous): 0.04695 g; KCl: 0.2 g; NaCl: 7.0 g; $NaH_2PO_4$ (monobasic): 0.1739 g; lactalbumin hydrolysate: 6.5 g; yeast extract: 5.0 g, lactose: 10 g, manganese chloride: 1 mg; plus sodium bicarbonate or another buffer such as Tris or HEPES. To these components is added 1 L water, and, while stirring, a small amount of xanthone and phenothiazine powder should be added. Growth may be improved by adding sodium arachidonate and lipoxidase (Sigma, soybean origin). Once dissolved, the medium should be adjusted to pH 7.5, though it has been found that the optimum pH for differing isolates varies slightly. The pH-adjusted medium should be sterile filtered or autoclaved and then stored at 4° C. This medium allows for growth and maintenance of HBB in culture for at least six months at 4° C.

An alternative medium, referred to as medium O, replaces the sugars in medium L, above, with 4 g glucose, 4 g fructose, 4 g sucrose, eliminating the buffer, xanthone, phenothiazine, arachidonate and lipoxidase. Medium L generally allows for better growth of HBB, but with some strains medium O has been better.

Dilution of medium L or medium O to a half concentration with water occasionally allows for better growth, with an enhanced visibility of organisms due to their swelling to a larger size. However, a problem of precipitate formation developed when using these diluted media. It was found that diluting the medium with normal saline instead of water reduced the precipitation but did not entirely eliminate it. Another alternative culture medium is RPMI-1640 cell culture medium, as well as several related media such as Dulbecco's, Iscove's and McCoy's. Greater growth is achieved with the addition of 5–10 mM pyruvate when grown under a grow-light

EXAMPLE 6
Physical Characteristics

Figure 3:
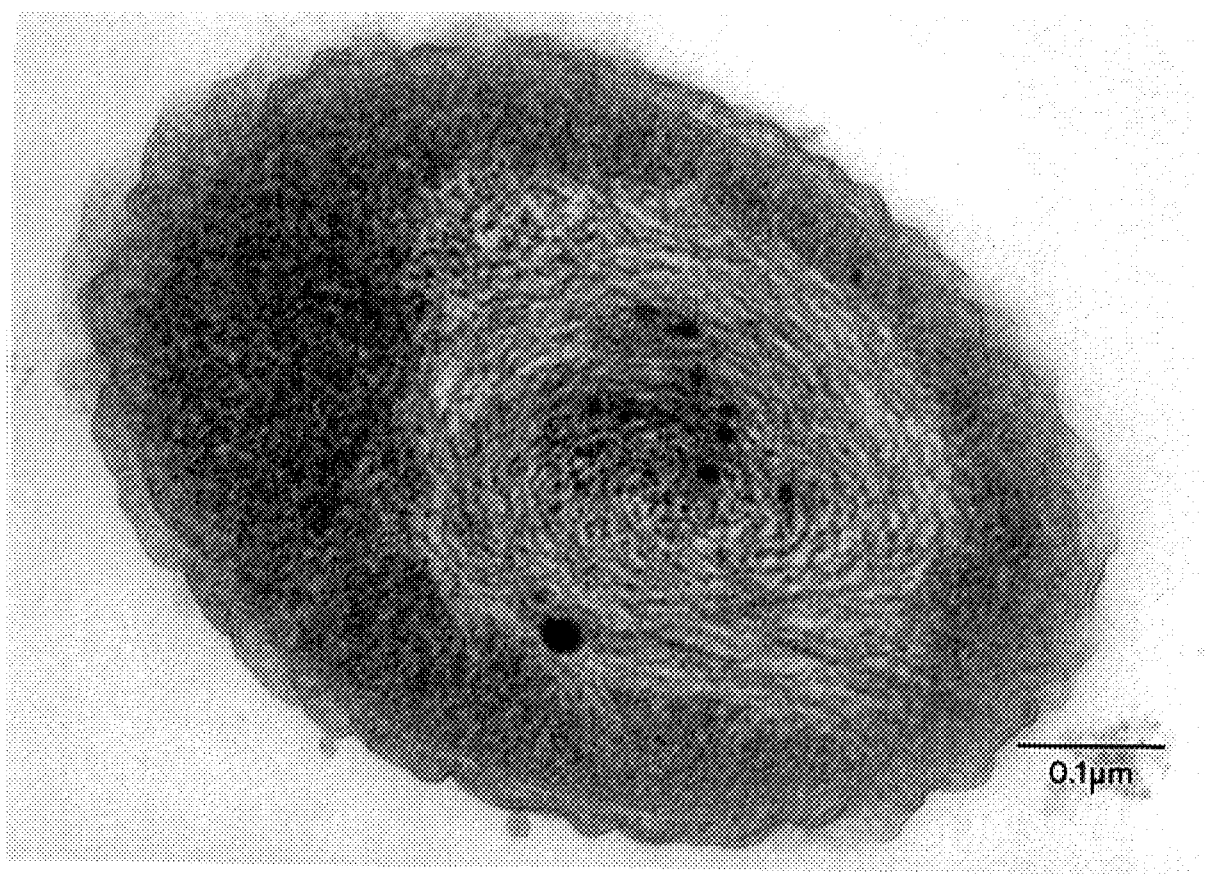
FIG. 3 is a transmission electron micrograph of human blood bacterium isolated from a patient with chronic fatigue syndrome. A single organism is shown, demonstrating a gram negative wall structure with a wavy outer membrane. The nucleoid is seen centrally and there is some extracellular material that presumably represents the slime material. Magnification approx. 150,000x.
Figure 4:
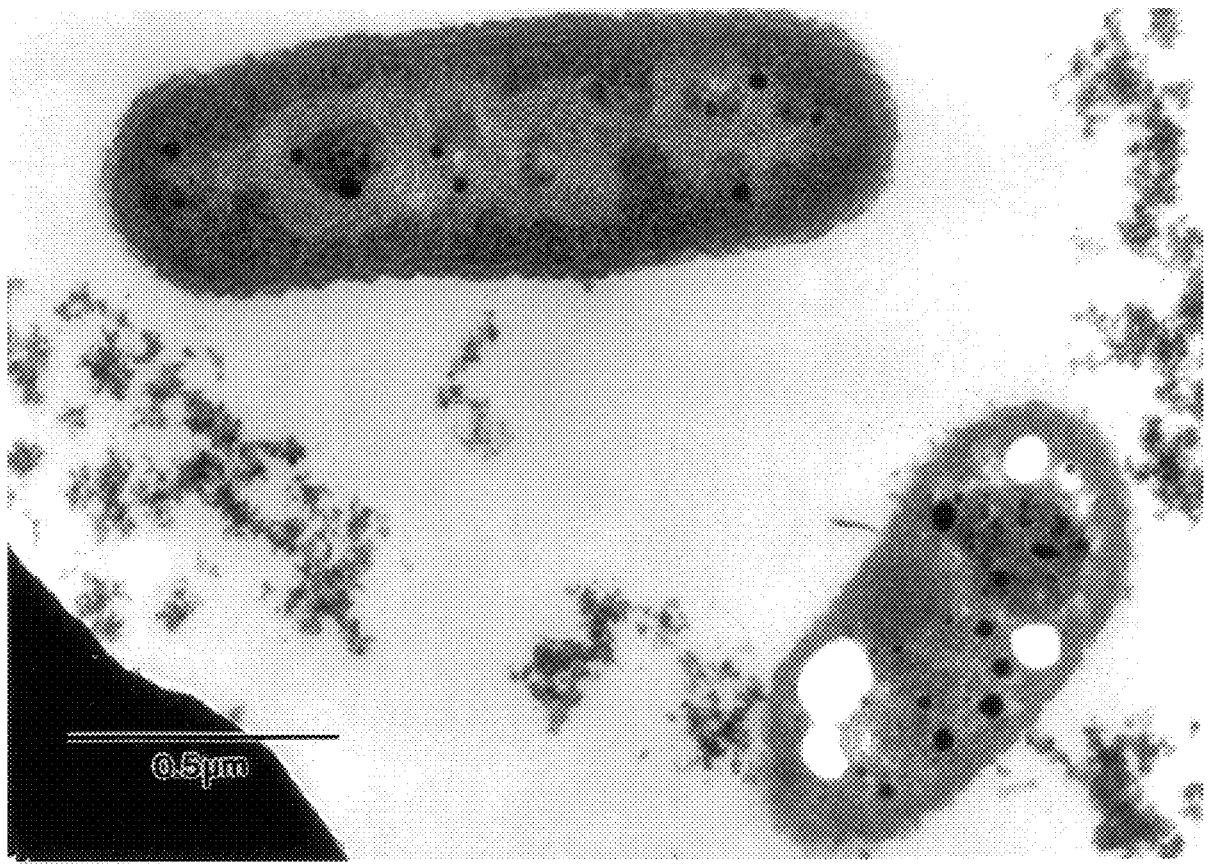
FIG. 4 is a transmission electron micrograph of human blood bacterium isolated from a patient with chronic fatigue syndrome. Two organisms are shown, one demonstrating features similar to the organism pictured in FIG. 3, the other showing transparent vacuoles and surface projections that could represent pili, conjugation tubes, or filamentous phages. Both contain small dense inclusions. There is some extracellular material that presumably represents the slime material. Magnification approx. 75,000x.

Morphology: HBB has been found to be extremely pleomorphic by phase contrast microscopy (1). When not dividing—i.e., under relatively static conditions including when viewed directly in blood—HBB appears as a long, flexible, often serpiginous rod, up to 15 microns or more in length. The ends of the rod sometimes appear swollen. When dividing, the bacterium is much shorter, typically becoming a coccus (FIG. 1). The diameter of the cells vary during the lifecycle, tending to be smaller when actively growing. At the smallest, they barely can be resolved with a 40X objective. HBB is gram variable, not acid fast. No capsules or flagellae have been observed by normal staining methods (1), although the Hiss stain does demonstrate extracellular material that is presumed to be a polysaccharide or polysaccharide-rich material (slime). There appear to be no included pigments. The presence of nucleic acids has been confirmed by staining of fixed organisms with acridine orange, with 4,6 diamidino-2-phenylindole or with the Bac-Light stain (Molecular Probes, Inc.) and viewing with a fluorescence microscope. The Bac-Light stain also confirms viability of the organisms. Transmission electron microscopy (1) of multiple isolates clearly demonstrates a gram negative wall structure, with a wavy outer membrane (FIG. 3), possibly with an S-layer, with stainable granular material between the inner and outer membranes, absence of flagellae or an outer sheath, with a clearly demonstrated nucleoid and several types of inclusions, including clear, lipid-like inclusions that probably represent poly-betahydroxybutyrate and electron-dense inclusions that are currently not further characterized. Some micrographs demonstrate linear protrusions from the surface that could represent pili, conjugation tubes, or linear phages (FIG. 4). Extracellular material is seen that probably represents polysaccharide or glycoprotein, but a true capsule was not seen. Although a spore-like state appears to exist, no true spores have been demonstrated by electron microscopy. In cultures grown in RPMI-1640, some of the bacteria seem to lack cell walls, while in 1/2 strength medium O the wall thickness varies in specific isolates and is sometimes thicker than normal.

What appear to be cell-wall-defective forms are often prominent in culture, and can appear as anything from swollen cocci to irregularly budding forms resembling budding yeasts to large spheroids. The tendency of HBB to form defective forms depends in part on the patient from which the HBB were isolated and in part on subsequent culture conditions. Defective forms vary over time in the patient as changes are made in the patient's nutritional status or as antibiotics are administered, suggesting that the defective forms may be a function of nutritional limitations.

Refractile inclusions are often present in HBB, observed by light microscopy, especially with phase contrast. These inclusions, like the cell wall-defective forms, also depend on the culture conditions and the patient source. The inclusions have not yet been fully characterized. Staining with Loeffler's methylene blue and toluidine blue shows some metachromasia (2). Alcoholic or glycolic sudan black stain (3) suggests that the inclusions contain both polybetahydroxybutyrate and pyrophosphate. Extracellular crystals are sometimes seen that are bipyramidal and acid soluble, suggesting calcium oxalate and that some of the intracellular inclusions could be calcium oxalate. There is apparent spore formation as demonstrated by Wirtz and Conklin stain (2). No true capsules are seen by crystal violet-copper sulfate staining (2). The cell wall defective forms in particular often contain large highly refractile inclusions. Some of the large, spherical, highly-refractive forms appear to have thick walls when viewed by phase contrast microscopy, which again suggests spore formation. Other evidence suggesting a spore-like state includes relative heat and radiation resistance (e.g., at 50° C. for seven days) and persistence of viable organisms that can be subcultured from flasks that have been in an incubator up to two years without adding fresh medium.

Large quantities of an extracellular "slime" or exudate are produced under some culture conditions. Microscopically, the exudate can form a fibrillar meshwork that completely obscures the organisms. The material binds the HBB cells together in clumps.

Though the HBB cells at times assume a yeast-like morphology, experiments suggest that the yeast-like cells are cell-wall defective bacterium, not yeast. For example, there is no growth of yeast-like forms in Sabouraud's medium (seven isolates, six months at room temperature), and no suppression by amphotericin B, miconazole, clotrimazole, sodium undecylate, sodium benzoate, sodium propionate, or nystatin. There appears to be no formation of hyphae. Additionally, the organism is not present in culture immediately after filtration through a 1.2 micron membrane filter, but "returns" after subsequent incubation. Further, the "yeast-like" cells are uniformly present and identifiable in all HBB isolates from blood, although in varying number. Moreover, there is an apparent transitional form between typical bacteria and the yeast-like forms. Staining with calcofluor white (0.01% in water) is weak and inconsistent; similarly, poor staining is obtained with periodic acid-Schiff's stain and with methenamine silver (3–4).

Motility: The motility of HBB in culture is partially dependent on the culture conditions. Under conditions where growth is limited but activity is stimulated by pyruvate or when freshly isolated from the blood, the rods show continuous active bending—definitely not the type of motility seen with ordinary flagellae or with spirochetes. Motility appears to be stimulated by pyruvate. It has not been possible to grow colonies as HBB actively penetrate 1.5% agarose, medium O for substantial distances. Higher agar concentrations cause the HBB to spread on the agar surface. This spreading indicates a possible gliding motility. The fact of this active motility, coupled with the glycocalyx, may explain why the HBB do not get trapped in clots during isolation from blood.

A few cultures viewed by vital staining of live organisms with Bac-Light stain (Molecular Probes, Inc.) have shown a different type of motility in a small percentage of the organisms. These show much more rapid movement of the type that is expected with flagellae. The presence of flagellae has not been confirmed by electron microscopy, but it is possible that the bacterium may be able to produce flagellae under appropriate conditions.

EXAMPLE 7

Chemical Reactions

There appears to be a remarkable paucity of identifiable chemical reactions. Despite the apparent use of sugars, very little pH shift occurs over time, and the shift may be either to a slightly acid or slightly basic. The only reactions that have been demonstrated consistently are hippurate hydrolysis, a relatively nonspecific phosphatase/DNAse activity and acetate esterase. A blue color change is produced in the presence of gold chloride, the chemistry of which is unknown; a weaker, brown color change is seen with silver nitrate. HBB make an extracellular exudate or gel. The exudate appears to be composed largely or entirely of complex carbohydrate. It is assumed that the extracellular material is very important to the pathogenicity of HBB in vivo, and that some of the immune reactions that lead to the diseases observed and associated with HBB may be against the exudate rather than against the HBB organism proper. Alternatively, the exudate may protect the bacteria from serum factors such as complement and antibody.

The amount of the exudate produced is strongly influenced by or dependent upon the composition of the culture medium. The current medium formulae (L and O) have been designed to reduce slime production. In the original, crude medium, a centrifuged culture may consist of more than 10% of this gel by volume. In the L and O media, older cultures of HBB may develop a thin layer of gel that traps the cells and makes them adherent to the culture flask. It has been observed that lectins that bind sialic acid, including wheat germ agglutinin, Maackia amurensis I, and Sambucus nigra, bind to this material and the bacteria; however, most lectins binding other sugars, including Maackia II, soybean, Dolichos bifloris, peanut agglutinin, Phaseolus vulgaris leukoagglutinin and erythroagglutinin, succinylated wheat germ agglutinin, Sophora japonicum, Bandeirea (Griffonia) simplicifolia I and II, Erythrina cristagalli, Pisum sativa, Lens culinaris, Datura stramonium, Jacalin, Lycopersicon esculentum, Solanum tuberosum, and Vicia villosa, do not appear to bind.

The following data summarize observed chemical reactions (referred to the methods in Refs.1–2). There was no significant acid or base production over a long time scale (>40 isolates), no color change with $FeCl_3$ addition (negative for deamination of several amino acids (9 strains)), Voges-Proskauer weakly positive (7 of 8 strains), Urease-deamination (by Nessler's reagent)-trace positive (7 of 8 strains), Esculin not hydrolysed (9 strains), Hippurate hydrolysed (9 strains), Nitrate not reduced (9 strains), no hydrolysis of ONPG (2 mg/ml) (4 strains), p-nitrophenyl acetate (1/6 saturated) hydrolysed (4 strains), though weak reaction seen with control, o-nitrophenyl caprate (1/6 saturated) not hydrolysed (4 strains), p-nitrophenyl phosphate (2 mg/ml) hydrolysed (4 strains), bis-p-nitrophenyl phosphate (2 mg/ml) hydrolysed (4 strains), DNA-methyl green (50 $\mu$g/ml) hydrolysed (4 strains), p-nitrophenylphosphoryl choline (2 mg/ml) hydrolysed (4 strains), Oxidase positive (3 of 5 strains, relatively weak), catalase (2 of 2 strains, weakly positive) and no reaction with triphenyltetrazolium chloride (500 $\mu$g/ml) (10 isolates)

EXAMPLE 8

Antibiotic Sensitivities

Antibiotic sensitivity is a problem characteristic with HBB: very simply, HBB are resistant to almost everything, making the development of a treatment regimen extremely difficult. Some strains seem to be relatively sensitive to penicillin G or V, and are even more sensitive when supplemented with clavulanic acid-containing Augmentin in vivo, likely due to an inducible beta-lactamase. Some positive clinical results have been observed with a combination of penicillin, probenecid, and Augmentin; the Augmentin is added to provide a beta-lactamase inhibitor. There is less sensitivity to amoxicillin and generally to the oxacillin group; however occasional isolates show higher sensitivity to oxacillin or cloxacillin. Some strains are sensitive to ciprofloxacin. Relatively little testing has been done with relatives of cipro, and HBB uniformly has shown resistance to aminoglycosides, sulfas, and trimethoprim. HBB is resistant to erythromycin, but some strains show sensitivity to clarithromycin and/or azithromycin. In addition, HBB appears to be resistant to most cephalosporins, but a few isolates show sensitivity to third generation cephalosporins only. A few of the HBB strains have shown limited sensitivity to doxycycline/minocycline.

An interesting feature is that some isolates are sensitive to isoniazid, though there is no reason to think that HBB is a mycobacterium, which is the only bacterium with which isoniazid is normally used. The isoniazid sensitivity may be related to the drug binding to a catalase/peroxidase-like enzyme in HBB as it has been shown to do in M. tuberculosis; thus, there may be a critical oxidative enzyme associated with the HBB that is similar to the M. tuberculosis catalase/peroxidase.

Sulfhydryl agents sometimes inhibit growth of HBB, consistent with the suggestion of a critical oxidative feature, but consistent with metal ion requirements as well. Treatment of patients with the antibiotics found to be effective on HBB does not eliminate the organism from the bloodstream; however levels of the HBB in blood can be suppressed in some patients. These suppressed levels of HBB correlate with the suppression of pathophysiologic symptoms. From the data, it appears that antibiotic sensitivity is not a simple phenomenon but that other factors in the patient, including nutritional factors, play a role.

The antibiotic resistance of HBB may be exploited for selective isolation from nonsterile sites. In addition, HBB resist all detergents tested; namely, 0.1% bovine bile, 0.1% Brij-35, 0.1% n-laurylsarcosine, 0.1% NP-40, 0.1% Triton X, 0.1% Tween-20, with the exception of 0.1% SDS, which does cause lysis. Additionally, HBB is resistant to 1:1000 benzalkonium chloride saturated hex achlorophene and 0.05% saponin.

The following data summarize observed antibiotic and antifungal sensitivities: amikacin (2 $\mu$g/ml)- no effect (1 isolate); 5–10 aminosalicylic acid (20 $\mu$g/ml)- no effect (4 isolates); amphoptericin (0.25 $\mu$g/ml)- no effect (1 isolate); azothromycin (0.25 $\mu$g/ml)- no effect (6 isolates), sensitive (7 isolates); cephalexin (2 $\mu$g/ml)- no effect (1 isolate); cefadroxil (4 $\mu$g/ml)- no effect (1 isolate); cefixime (2 $\mu$g/ml)- no effect (8 isolates), sensitive (5 isolates); ciprofloxacin (1–2 $\mu$g/ml)- no effect (5 isolates), partially sensitive (1 isolate), sensitive (1 isolate); clindamycin (2.5 $\mu$g/ml)- no effect (1 isolate); clotrimazol (1/10 saturated)- no effect (1 isolate); cloxacillin (2 $\mu$g/ml)- no effect (16 isolates), sensitive (5 isolates), growth stimulated (6 isolates); dapsone (1/20 saturated)- no effect (1 isolate); furazolidone (1/20 saturated)- no effect (1 isolate); gentamycin (2 $\mu$g/ml)- no effect (1 isolate); isoniazid (2 $\mu$g/ml)- no effect (24 isolates), sensitive (5 isolates), growth stimulated (6 solates); miconazol (1/10 saturated)- no effect (1 isolate); minocycline (1–2 $\mu$g/ml)- no effect (29 isolates), sensitive (12 isolates), growth stimulated (4 isolates); nalidixic acid (4 $\mu$g/ml)- no effect (1 isolate); nystatin (saturated)- no effect (1 isolate); ofloxacin (1/20 saturated)- no effect (1 isolate); penicillin V (1–2 $\mu$g/ml)- no effect (27 isolates), sensitive (17 isolates), growth stimulated (4 isolates); primaquine (2 $\mu$g/ml)- no effect (31 isolates), sensitive (15 isolates), growth stimulated (1 isolate); quinacrine (2 $\mu$g/ml)- no effect (1 isolate); rifampicin (1/200–1/10 saturated)- no effect (18 isolates), sensitive (7 isolates); sodium benzoate (50 $\mu$g/ml)- no effect (1 effect); sodium propionate (50–250 $\mu$g/ml)- no effect (2 isolates); • sodium undecylate (50 $\mu$g/ml)- no effect (1 isolate); spectinomycin (4 $\mu$g/ml)- (1 isolate); sulfamethoxazole - no effect (1 isolate); sulfapyridine (1/10 saturated)- no effect (6 isolates), no effect (1 isolate); sulfasalazine (1/10 saturated)- no effect (6 isolates), no effect (isolate); tolnaftate (2 $\mu$g/ml)- no effect (1 isolate); trimethoprim (1/20 saturated)- no effect (1 isolate); vancomycin (2 $\mu$g/ml)- no effect (1 isolate).

EXAMPLE 9

Sequence Analysis and Classification

The entire 16S rRNA gene (Rb 16S rRNA: SEQ ID NO: 1 and 58 16S rRNA: SEQ ID NO: 2), most of the 23S rRNA gene (Rb 23S rRNA: SEQ ID NO: 3 and 58 23S rRNA: SEQ ID NO: 4) and most of the intergenic spacer region between 16S and 23S (SEQ ID NO: 5) have been collected. Preliminary sequence data of a gene encoding a putative multidrug resistance protein is also shown (SEQ ID NO: 6). These data were produced from DNA isolated from cells cultured using either 1/2 O medium or modified RPMI medium.

For the 16S sequence data, DNA was amplified using both 16S rRNA universal and specific primers designed from literature searches (GAGTTTGATCCTGGCTCAGAACGAACGCTGG, SEQ ID No: 7 and sequence of 1208 base pairs (bp) was obtained from a control sample and has been completed in both directions with overlaps (SEQ ID NO: 1). Different isolates produce DNA that aligns with different strains of Methylobacterium. Methylobacterium is a chlorine-resistant, pink-pigmented bacteria isolated from a number of sources including water and soil. This gram-negative rod was identified as a member of the genus Pseudomonas on the basis of physiological traits but has been reclassified. Recently there have been a number of Methylobacterium isolated from clinical specimens.

The strain having the most prevalent homology (99%) compared to the presently disclosed Rb 16S rRNA sequence is Methylobacterium organophilium with a difference by only 5 bases (1184 bp out of 1189 bp are the same). The remaining 19 bp of the 1208 bp are not found in the published sequence from GenBank. Other strains sequenced from different patients have been similar, however, not identical to Methylobacterium organophilium. These sequences are similar to strains 05, strain 15 and strain 73. The second 16S rRNA sequence obtained from a patient (namely 58 16S rRNA, SEQ ID NO: 2) contains 1502 bp and is most similar to Methylobacterium sp. (strain F05). The published sequence for Methylobacterium sp. (strain F05) is 1405 bp long or approximately 100 bp shorter than the presently disclosed 58 16S rRNA sequence, wherein the sequence of 58 16S rRNA of HBB is 99% identical to strain F05 (1398 bp out of 1403 bp are identical). The two sequences Rb and 58 for 16S rRNA gene differ from each other by 4% with different base pairs from 1167 to 1208.

The significance of this strain variation between control samples and patients has not yet been established. It is possible that some strains are pathogenic and others are not. Whether the sequenced HBB is a modified form of these listed strains is unknown. However, HBB appears to be different morphologically and in terms of growth requirements from a strain obtained from ATCC. The fact that HBB is able to survive in the blood stream would require some modification from the wild-type strain. Analysis of the genome may demonstrate the presence of a pathogenicity island(s) or other transmissible genetic element(s). These elements may have been acquired by Methylobacterium through horizontal gene transfer during microbial evolution leading to the creation of HBB.

The 23S rRNA sequence obtained to date includes 2542 bp (Rb 23S rRNA: SEQ ID NO: 3). About ¾'s of the length has been sequenced in both directions, however there are areas where the sequence abuts without overlap. This sequence, aligns with about 90% similarity to the 23S rRNA gene for Rhodopseudomonas palustris, which is the most closely related alpha proteobacterium with published data on the 23S gene. Sequence data from a control sample, Rb 23S rRNA (SEQ ID NO: 3) and from a patient sample, 58 23S rRNA (SEQ ID NO: 4) were obtained. The two sequences Rb and 58 for 23S rRNA differ from each other by 5% (1903 bp out of 1996 bp are identical) with 6 gaps. Primer pairs used for 23S rRNA PCR reactions were constructed: CCGAATGGGGVAACCC (SEQ ID No: 9) and TCGACCAAGAGRRGCTTT(SEQ ID No: 10); TAGCTG-GTTCTCYYCGAA (SEQ ID No: 11) and GGCAT-TGAAGCCCTCTTCC (SEQ ID No: 12); AAACCGACA-CAGGTRG (SEQ ID No:13) and CGACTTYCGTAGATTC (SEQ ID No:14) (Ludwig et al.).

The intergenic spacer region (IGS) found between the 16S and the 23S gene was obtained from a control sample and sequenced (Rb IGS: SEQ ID NO: 5) using primers designed from the two above sequences (ACGGTAGGGTCAGCGAC, SEQ ID No:15 and CCTCCCAGCTTCCACCC, SEQ ID No:16). It contains 836 bps that align poorly to a number of IGS genes. There are very few homologies in the database with Bradyrhizobium japonicum, another alpha proteobacterium being the most closely related. The area of the bacterial genome is not well conserved between species and should provide ample opportunities for the design of very specific primers for DNA based diagnostics including PCR and in situ hybrizations.

A sequence produced from a set of PCR primers specific for a family of Methylobacterium genes was obtained from a control sample (namely drug resistance protein gene, SEQ ID NO: 6). The primers used are ATGTCCTGCGTGTCT-GCA (SEQ ID No:17) and GTACTAGTCCAGCGTGTC (SEQ ID No:18). This sequence does not match any known sequence in the database, but when translated to protein is a close match for a multidrug resistant protein from Bradyrhizobium japonicum.

The 16S rRNA sequence (SEQ ID NO: 1) establishes the bacterium as a member of the genus Methylobacterium. The reported members of this genus are able to grow on media which provide the carbon source from methyl compounds such as methanol, formaldehyde, formate, methylamine, etc. They are facultative in their carbon sources, and can utilize sugars and a variety of nitrogen sources. Significant growth of HBB has not been obtained using the various media used for continuous culture of the defined Methylobacterium species. Addition of various methyl compounds such as methanol, methyl acetate, trimethylamine and trimethyl phosphate to 1/2 strength medium O or RPMI has produced minimal or no stimulation of growth. Methylobacterium has on rare occasions been reported from immunosuppressed humans, but is not ordinarily isolated from human or mammalian sources. Instead, it is ordinarily isolated from environmental sources such as bodies of water. Thus HBB significantly differs from any known Methylobacterium isolates Very little is known about the strain differences of HBB. There appear to be consistent morphologic differences from different patients. Antigenic characterization has not been examined. Patterns of antibiotic sensitivity suggest that certain antibiotic sensitivities may be more frequent with certain diagnoses.

EXAMPLE 10
In situ Hybridization

Figure 5:
FIG. 5 shows human blood bacterium isolated from a culture of a patient with multiple sclerosis. The bacterium is hybridized with a Methylobacterium-specific rhodamine-labeled probe. The probe is bound to a diploid rod apparently in division. Magnification approx. 1,250x.
Figure 6:
FIG. 6 is a photograph of the same microscopic field as the one shown in FIG. 5. It shows that the diploid rod is positive for the counterstain 4',6'-diamidino-2-phenylindole.2HCl (DAPI). DAPI binds only to nucleic acids and confirms the presence of bacteria. Magnification approx. 1,250x.

In situ hybridization was performed using probes specific for Rb 16S rRNA of Methylobacterium. Two probes were synthesized (TCGCAGTTCCACCAAC, SEQ ID No:19 and CTGTGGTTGAGCCACA, SEQ ID No:20), each of which are labeled on the 5' end with the fluorescent dye, rhodamine. Two other probes from the set of universal probes designed to bind all bacterial species were labeled with the fluorescent dye, fluorescein. When hybridized with cells from HBB culture, bacteria were bound by the probes from Rb 16S rRNA and were fluorescent orange indicating they were bound by the rhodamine-labeled probe (FIG. 5). E.coli was used as a control bacteria and did not bind the Methylobacterium-specific probe. A third dye, 4',6'-diamidino-2-phenylindole.2HCl (DAPI), was used to detect all cells containing DNA (FIG. 6). These results were consistant with PCR sequencing results and indicate that HBB is closely related to Methylobacterium.

EXAMPLE 11
Clinical Indications

Experiments have been conducted investigating the correlation of the presence of or increased presence of HBB with the clinical symptoms of three autoimmune diseases, and the results of instituting an antibiotic regimen in patients. Eighty patients were seen, 66 of whom received antibiotics long enough to allow clinical evaluation. The clinical evaluation was based principally on reported symptoms, although there was also objective evidence of improved function for some multiple sclerosis patients. All patients were cultured repeatedly to determine levels of HBB. The antibiotic treatment regimen was based on antibiotic sensitivities done on a pilot series of cultures and on the known properties of the organism, which clearly requires long-term, continuous treatment to address its very slow growth rate. This approach differs from usual treatment regimens for other bacterial infections. Neither the subjects nor the investigators were blind, and there was no untreated or placebo-treated control group.

Antibiotic treatment consisted of one or more of the following three antibiotic regimens: (1) penicillin V, 500 mg four times a day, plus probenecid, 500 mg four times a day, plus Augmentin 500 mg four times a day; (2) ciprofloxacin, 500 mg three times a day; or (3) isoniazid, 100 mg three times a day. Most patients received a combination of two of the regimens concurrently. Further, if a certain regimen did not appear to be effective or efficacy declined over the treatment period, the patient was often switched to a different regimen. None of the three regimens appeared to be significantly better or worse than the other two.

The 66 patients for whom follow-up was adequate are summarized below by diagnosis: Chronic fatigue syndrome: 41 patients total; 30 patients improved, 11 patients did not improve. Reduced levels of HBB were seen in all improved patients and HBB levels were not reduced in unimproved patients. Multiple sclerosis (typical): 7 patients total; 4 patients improved; 3 patients did not improve. Two of the four improved patients had marked functional improvement, for example, were able to walk with a cane where a wheelchair had been previously required. There were reduced levels of HBB in three of the improved patients, with an insufficient culture follow-up in the remaining improved patient. There was no reduction in HBB in the patients that remained unimproved. Atypical multiple sclerosis: One patient was tested and was markedly and objectively improved for five months before developing antibiotic resistance (resistance later documented with sensitivity testing). There was a reduced level of HBB during the period of improvement and a marked increase in HBB during relapse. Borderline diagnosis (either chronic fatigue syndrome or multiple sclerosis): Three patients were tested. All three patients improved, with reduced levels of HBB. Fibromyalgia (pure or associated with chronic fatigue): Three patients were tested, and all patients improved, with corresponding, reduced levels of HBB in the blood. Arthritis (rheumatoid or other): Five patients were tested; four improved and one did not improve. All improved patients demonstrated reduced levels of HBB in their blood, with no reduction in the level of HBB in the unimproved patient. Behcet's syndrome: One patient was tested and did not improve, and there was no reduction in the level of HBB in this patient's blood.

The striking feature of the treatment of these patients was that there was a 100% correlation between clinical improvement in the patient and reduction of the levels of HBB in the patient's bloodstream. This was true even though the improvement resulted from treatment with antibiotics—despite these illnesses never having been associated with a bacterial cause in the prior art.

Subsequent to this study, laboratory support has been supplied to various physicians treating patients. Results have been similar, except that the percentage of responding multiple sclerosis patients has appeared to be lower than the level that was seen in the small, initial group. Furthermore, one collaborator who has been treating chronic fatigue syndrome patients with penicillin and probenecid has reported about 100 patients who are in complete remission from symptoms. This correlates to about a 20% cure rate.

Clearly, the improvement in symptoms correlates with reduction in HBB in the bloodstream. Long-term follow-up has shown that for some of the responding patients of the original study, antibiotic resistance has developed, though each patient benefited greatly overall from treatment. Lately, study has also demonstrated an important phenomenon, that is, frequently when antibiotic resistance is present, the antibiotics can actually stimulate the growth of the bacteria. The mechanism for this effect is unknown, but it has been seen repeatedly both in culture and in patients. The increases in HBB when resistance is present have correlated with increased symptoms.

EXAMPLE 12

Treatment of HBB-Associated Disease

Most treatment information has been developed primarily from uncontrolled patient trials; however, in vitro sensitivity testing is routinely being done. One skilled in the art, on the other hand, recognizes that, as with all pharmaceutical preparations, in vitro and in vivo results do not correlate completely and dose and dosage regimens depend upon the nature of the disease, the stage of infection, the characteristics of the particular pharmacologic agent—e.g., its therapeutic index, the patient, the patient's history and other factors. A regime or schedule is continued to optimize effectiveness, balanced against negative effects of treatment. Sensitivity tests against the agents that show promise at this time are run routinely, and it is urged that this practice be continued in further testing, as patients have had contrary therapeutic results when treated with an antibiotic to which their isolate was resistant.

Several treatment regimens have been thoroughly tested and have shown value both when testing in vitro and in trials on patients in vivo. These regimens produced actual complete relief from the symptoms of chronic fatigue syndrome patients in a few months in a substantial minority of patients. In these trials, many patients experienced a significant improvement in symptoms but did not experience complete relief from symptoms, at least over the testing period of a few months. Additionally, there is long-term testing data with a few patients that suggests that long-term cure may occur after withdrawal of antibiotics even though organisms remain. Many patients do develop antibiotic resistance with time, and a proportion of patients do not respond at all—presumably a result of antibiotic resistance or of a rate of growth of the bacteria in these patients that outstrips the antibiotics.

With multiple sclerosis patients, less than 50% have responded positively to treatment. Further, complete recovery cannot be expected as some nervous system damage may have accrued prior to treatment and cannot be reversed; however, about 20% of patients had a definite improvement in motor function. It is yet undetermined whether the responsive individuals will remain improved indefinitely, or whether progression of the disease is altered after cessation of therapy, though several patients have maintained the improved level of function for several years.

With HBB, "true" cure—i.e., elimination of all bacteria—has not been achieved with the antibiotics that are available; and indeed, may not need to be as HBB appears to be present at some level in all human beings. However, control of HBB for a period of time long enough to allow healing to occur and/or the immune system to recover is clearly possible.

The following antibiotics have shown value in vivo to date; however the present invention should not be limited to the following treatment regimes as one skilled in the art of pharmacology would recognize a host of alternatives: Penicillins with probenecid: Clinical responses and culture tests suggest that response is best to the penicillin G/penicillin V spectrum. Clinical responses and failures indicate that HBB makes a penicillinase or general beta-lactamase, likely slowly inducible. Thus, penicillin alone is not effective for a sustained response in most patients, although it gives short-term response in many. The penicillinase can be inhibited by simultaneous administration of Augmentin (Clavulin; amoxicillin+clavulanic acid) or a penicillinase-resistant penicillin. The current recommendation for adults is a combination of oral penicillin V 500–1000 mg., Augmentin 500 mg., and probenecid 500 mg., all taken four times a day. A few patients have done better with dicloxacillin, but the majority of HBB isolates shows poorer sensitivity to this group of penicillins.

An alternative therapy to penicillins with probenecid, above, is administration of Ciprofloxacin in divided doses of 1–2 grams/day. The suggested dose for most adult patients is 500 mg three times a day. The effect of adding probencid to the regimen has not been tested; the probencid may reduce excretion and increase penetration of the CNS. If probenecid is given, it should be given at an approximate level of 500 mg three or four times daily. Since probenecid slightly raises blood and appears to raise the cerebrospinal fluid (CSF) level of ciprofloxacin, the dosage of ciprofloxacin may be reduced if probencid is used, perhaps to 250 mg three or four times daily. The effect of giving higher doses less often, e.g., 750 mg twice a day has not been tested. In theory, with HBB, it is better to give smaller, more frequent doses to maintain continuous blood levels. At a minimum, ciprofloxacin administration should be continued for at least two months, with continuous assessment of HBB levels and clinical response. Such treatment is very expensive and it is contraindicated in children. For patients who do not tolerate ciprofloxacin, another drug of the same group may be a viable alternative.

Yet a third alternative for treatment is administration of Isoniazid, 100 mg given three times a day. It is unclear why HBB is occasionally sensitive to Isoniazid, as it is not related to Mycobacterium. However, this anomaly is advantageous as Isoniazid is inexpensive and well-tolerated. Isoniazid must be administered with vitamin B-6 (pyridoxine) as it binds the vitamin in vivo and can lead to vitamin deficiency with peripheral neuropathy.

Third-generation cephalosporins appear to be an alternative; however, HBB is resistant to first- and second-generation cephalosporins. At present, sensitivity testing has been done with cefixime, and the normal maximum sustainable dosage is recommended. CNS penetration may be unreliable, and at least to this point, third-generation cephalosporins appear to be less efficacious than other drugs. Further, some data indicates that thirdgeneration cephalosporins may actually stimulate growth in culture.

Azithromycin and clarithromycin are additional alternate antibiotics. HBB is resistant to erythromycin. Data is limited on the results of treatment with azithromycin and clarithromycin, so an in vivo dosage has not been established. Clarithromycin appears more effective in culture, but in vivo, the tissue penetration capabilities of azithromycin appear to be important. However, as with third-generation cephalosporins, some data collected to date suggests that azithromycin and clarithromycin often stimulate growth. There appears to be a synergistic effect with a few isolates upon treatment with chloroquin and hydroxychloroquin.

Minocycline or doxycycline are alternate antibiotics; however, sensitivity to these drugs is less common than to the drugs listed above, and minocycline or doxycycline do not kill the bacteria so much as slow their growth. Doses have not been established; although, the normal maximum sustainable dosage is recommended.

Sporadic sensitivity to other drugs has been noted, but so far results do not appear to be consistent enough for general use, though routine experimentation is likely to result in the identification of additional effective antibiotics. Aminoglycosides and sulfa-trimethoprim have no effect on HBB in culture. Due to the requirement for long-term treatment, drugs that cannot b e administered orally have not been studied. Moreover, use of nutritional adjustments in combination with the antibiotics may generally improve results.

As a rule of thumb, therapy should be continued for a minimum of two months, with constant monitoring of HBB levels and clinical response. Longer treatment likely is needed in the majority of patients, particularly for MS patients. Treatment is complicated by the fact that the organism has so-called "resting forms" or possibly true spores and makes cell wall defective-forms which resist antibiotics in normal treatment schedules, requiring continuous high-dose antibiotics over a long period of time. Cautious withdrawal of drugs after several months after improvement has leveled off is recommended. Any treatment regimen should take into consideration drug risks known and published in the art, as well as in vitro sensitivities, clinical tolerance and economic considerations.

A factor in the long-term effect of treatment appears to be due to the restoration of efficacy of the patient's immune system. Symptoms likely are the result of immune reaction directed against HBB or a product thereof. The above regimens and others are likely to produce Candida overgrowth. These yeasts can usually be controlled with oral nystatin 500,000 U three or four times a day, Nizoral 200 mg once a day, or Diflucan 100 mg once a day. Nystatin only treats the GI tract, is appropriate for most males, and only may need to be prescribed for a few weeks. Nizoral produces a general effect and is suggested for women. Diflucan is one alternative to Nizoral and is safer, possibly more effective, but is more expensive.

Most responding patients have been found to have a pronounced Jarisch-Herxheimer reaction for the first few days or weeks of therapy. In theory, the Jarisch-Herxheimer reaction is due to the rapid death of organisms releasing internal contents that stimulates a short-term hypersensitivity response, and is presumably a sign of antibiotic sensitivity. The reaction should not be mistaken for a drug reaction or for an adverse response to therapy. The patients have been found to be more comfortable if a steroid is co-administered for a few days. Indeed, steroids may have an additional benefit as they may inhibit production of compounds that may stimulate growth of the bacteria. During the initial phase of treatment, depression may be a problem, and a few patients have complained of muscle cramping.

All drugs may produce allergic reactions, and some patients with increased levels of HBB have a much higher than usual incidence of drug allergies. Ciprofloxacin has been linked with rare but severe reactions such as liver or marrow failure and can be a problem to the kidney due to dehydration. Ciprofloxacin also produces photosensitivities and produces necrosis of cartilage in children and is contraindicated in children for this reason; there is a risk of damage to cartilage with long-term use in adults as well.

Probenecid is contraindicated in patients with kidney problems due to problems with dehydration. Likewise, Isoniazid produces rare severe hepatitis or very rare marrow failure, more often in older patients. GI complaints are occasionally seen with any antibiotic and can be severe enough to require a change of therapy. Pseudomembranous enterocolitis is a remote possibility. It is recommended that the CBC and liver, hepatic and renal functions be monitored periodically, initially every 3–4 weeks and whenever there are adverse symptoms. A few patients have shown unpredictable symptoms such as chest pain and tachycardia. It is likely that there is a low-grade myocarditis present in a few patients that is exacerbated with the antibiotics. Propranolol may help these symptoms as well as lessen the headaches that some patients experience. Some patients who do not tolerate therapy well have shown positive response utilizing a regime which starts with low dosage of the drug, continuing with gradual increases in dosage. When multiple drugs are being given, it may help to identify adverse and positive drug reactions if the drugs are started sequentially. If a patient does not respond after a reasonable trial (1–2 months) or if the patient's condition declines, the regime should be discontinued. There have been rare cases where patients did not respond until more than a month of treatment, but studies thus far show overwhelmingly that patients respond within weeks of treatment.

Ongoing inflammation and/or stress promotes the growth of HBB, related in part to release of arachidonate derivatives. NSAIDs have a limited role; particularly ibuprofen which produces symptomatic improvement and some reduction in bacterial levels. Control of stress and other infections is an adjunct to treatment. It is likely that a major site of infection with HBB is the mouth, especially the gingiva. Many patients give a history of symptoms beginning shortly after dental problems, especially abscesses and root canals, or of flareups when dental problems developed. It is important that the patient be surveyed to be sure that there are no lurking dental infections and that any problems that are present be corrected.

An important aspect of the present invention is that HBB is present in all "normal" persons and appears in increased levels in persons with nonspecific symptoms or individuals having any one of a number of clinical disorders including chronic fatigue and immune dysfunction syndrome (CFIDS), fibromyalgia, and several autoimmune disorders such as multiple sclerosis, lupus erythematosis, and rheumatoid arthritis. There is a definite positive correlation between reduction in HBB counts in patients on an appropriate antibiotic regimen and significant improvement in symptoms.

For many patients, antibiotic therapy may not be appropriate or may not be possible, but it may be possible to partially control the level of the bacteria by nutritional measures. As is known generally, persons who are ill should attempt to maintain good nutrition. Some of the following guidelines are suggestions that have been previously made in the CFIDS literature; and many have been derived from direct experiments in culture.

Many patients have observed that high-dose vitamins make them feel better. There is no evidence that the bacteria are dependent on externally-provided vitamins; thus, there is no reason not to take them. A good multivitamin containing higher than normal levels of the B vitamins, especially vitamin B-6 and folic acid, vitamin C, and possibly vitamin E is recommended. Vitamins A and D can produce toxicity at significantly higher than normal levels so an excess should be avoided, but some supplementation may be good. Of course, very large doses of certain of the B vitamins, vitamin C and vitamin E also can be toxic, so there is a limit to how much of any of the vitamins should be taken. It is recommended that vitamins with multiple minerals be avoided, as certain of the minerals discussed below may be a problem. Some patients have reported improvement in symptoms from vitamin B-12 injections. These are usually administered by a physician. Supplementation with niacin (or nicotinic acid, not niacinamide or nicotinamide), B-6 (pyridoxine), B-12 and folic acid may be particularly important in persons using cysteine (cystine) supplements.

The CFIDS literature suggests that there may be improvement from injections of magnesium sulfate and oral zinc supplements. Results obtained in studies in the present invention indicate that increased levels of magnesium have little effect on the growth of the bacteria. Presumably the reported effects of magnesium are due to a secondary effect on symptoms. Supplementation with oral magnesium is a possibility, but dosage should be monitored, particularly if the magnesium is not taken in combination with calcium. Magnesium compounds are laxatives at oral doses over a few hundred milligrams at a time.

Testing indicates that the growth of HBB is stimulated by compounds of copper, manganese, tin, iron and possibly other metals including aluminum, silver and mercury, suggesting that mineral supplements containing these minerals, as well as foods that are high in these minerals, should be avoided. It is likely that copper and iron are the most significant.

Both stress in general and inflammatory processes in particular stimulate the growth of the bacteria. Inflammation results in the release of several copper and manganese-containing enzymes from white blood cells and raises blood copper levels. Inflammation, stress, and certain hormones all elevate blood levels of copper, mostly bound to a specific protein; thus a reduced intake of foods high in copper, particularly shrimp, lobster, crab, crayfish, and liver is indicated. On the other hand, an increased intake of zinc is recommended, as zinc suppresses the growth of these bacteria in culture and increased zinc intake competes with some of the other minerals that have been indicated as being a problem. Zinc also has a beneficial effect on the immune system in general, which is why it was originally recommended. The recommended amount is 25 mg a day of zinc as zinc sulfate or an equivalent zinc compound for the average adult. Amounts over that can lead to overdosage.

Overdosage of zinc produces anemia and weakness because excessive reduction of available copper interferes with the body's ability to make enzymes that supply the bulk of the energy to cells in the body. Further, zinc can interfere with the incorporation of iron into the hemoglobin in red blood. Again, zinc levels, as well as iron levels in the blood, should be monitored closely. An additional reason for monitoring iron levels is that there is a possibility that iron stimulates bacterial growth. The best test for total body iron stores is the serum ferritin, and it is recommended that the iron level b e kept at the lower end of the normal range.

Another trace metal that has been suggested as beneficial in the CFIDS literature is chromium. Testing indicated no inhibition of bacterial growth by chromium, and, in fact, indicated that chromium possibly stimulates some strain. Chromium is known to be needed for insulin activity. Further, many CFIDS patients have sugar cravings and increasing fatigue several hours after eating. Chromium antagonizes this state. Since increased zinc will probably antagonize absorbtion of chromium, some chromium supplementation along with zinc is probably needed, at a dosage of 100–200 mg per day. Chromium also reduces the risk of arteriosclerosis.

Further, CFIDS literature suggests that certain sulfur-containing compounds may be beneficial. Garlic in particular has been mentioned, and one patient consumed large amounts and was convinced that it helped his symptoms. The compound that gives garlic its characteristic odor is one of these sulfur-containing compounds. These compounds react with several metals within the body, including copper, and therefore may be complementing zinc. The active compounds have a substantial odor; however, the garlic powders and oils that have been deodorized may lack the active sulfur compounds. Onions and other relatives of garlic may have the same benefits.

Experiments on the effect of sulfhydryl reagents suggest other compounds may have at least as much value as garlic, but also suggest that some sulfhydryl compounds may sometimes be contraindicated. The effects of 1-cysteine (cystine), an amino acid that is one of the basic building blocks of proteins, has been studied. The amount of cysteine in the diet affects the availability of other amino acids through various metabolic interactions. Increased cysteine clearly suppresses growth of some strains of HBB in cultures, but stimulates other strains. Cysteine is a minor component of almost all proteins, but is present in quantity in only a few sources. A daily cysteine (cystine) supplementation of 500 mg/day is suggested—not higher—and only in those patients whose isolate shows inhibition by cysteine in culture. Additionally, cysteine (cystine) should not be taken at the same time as zinc, calcium, or magnesium supplements, as that might interfere with the absorbtion of one of the metals.

In rare individuals the kidney has a problem handling cystine, and it is excreted in amounts so high that the cysteine crystallizes in the urine. Thus, supplementation could lead to the formation of kidney stones. Persons with a diagnosis of cystinuria should not take supplemental amounts, and microscopic urinalysis is recommended after treatment with supplements. Maintenance of good hydration will help with this potential problem.

The CFIDS literature suggests that taurine may be beneficial. In the testing to date, taurine has no effect on cultures. In the body cysteine is converted to taurine. Taurine may be inhibiting the breakdown of cysteine.

HBB growth is somehow tied directly to the inflammatory process. Isolates of the bacteria from patients who have been stressed, are ill, or who have active inflammatory processes, show not only greater numbers of organisms, but also display organisms with a much greater growth potential in culture which subsides over time. Apparently the growth of the bacteria is affected by the availability of derivatives of unsaturated fatty acids that are produced as part of inflammation.

The critical material(s) for HBB growth are presumably derived from an unsaturated fatty acid known as arachidonic acid that is released as one of the primary products in the inflammatory process. Arachidonic acid is a normal and necessary component of the body and can be derived from the diet directly or synthesized in the body from other unsaturated omega-6 fatty acids. Many antiinflammatory drugs such as aspirin and its relatives block the conversion of arachidonic acid to certain compounds that are effective mediators of inflammation. Unfortunately, these drugs block some of the possible conversions but not all, and administration of most drugs in this class has not produced much effect on HBB or the symptoms of the patients.

Steroids partially block the release of free arachidonic acid. Steroids have been used for a long time in the treatment of various "autoimmune" disorders including lupus erythematosis, rheumatoid arthritis, and multiple sclerosis, all of which are related to HBB. However, steroids are not a cure-all, and there are many complications and side effects associated with their use, nor do they block the conversion to arachidonic acid completely. It is possible that the beneficial effect of the steroids is related directly to suppression of growth of the bacteria, rather than merely suppressing inflammation.

Ibuprofen may partially block this process and its use at a moderate level should be considered, taking into consideration the risks of long-term use. In any case, obviously, the first consideration in treatment should be to control any treatable inflammatory processes that exist in the body and to control infection and inflammation in general, no matter what the source. This includes a general control of stress. It has been well-documented that CFIDS and MS patients tend to worsen in general as physical or mental stress or illness occurs.

Another dietary adjustment that can be made to decrease the amount of arachidonic acid that is available to be released in the body is to restrict the dietary intake of fatty acids. Fat intake in general should be reduced, particularly the intake of most cooking oils and margarines. Additionally, CFIDS literature suggests that supplementation with carnitine helps some patients. Carnitine plays a role in the metabolism of fatty acids, so it may affect the availability of arachidonic acid. At this time, carnitine supplements are not recommended A large portion of the patients tested are partially or completely resistant to the available antibiotics. In general, these patients have the highest levels of bacteria and their bacteria show the greatest growth potential in culture. Nutritional manipulation to slow the growth of bacteria based on dietary supplementation with vitamins (increased B vitamins, C, and E but not A and D), zinc 25–50 mg/day, chromium 100–200 mcg/day, sulfhydryl compounds such as cystine 500 mg/day and garlic, appropriate sources of non omega-6 unsaturated fatty acids (at least 5000 mg per day), elimination of undesirable foods, particularly those containing high levels of copper and omega-6 unsaturated fatty acids, and reduction of iron levels may convert some of these untreatable patients into responders or at least will reduce the severity of their clinical problems.

EXAMPLE 13

Detection and Diagnosis

HBB can be quantified to diagnose disease and evaluate efficacy of course of antibiotic treatment. These procedures are those known in the art and include uses of antibodies and DNA probes, Western and Southern blots, PCR and the diagnostic kits therefor. First, organisms can be quantified by culture. This has been done successfully by microscopic counting of organisms within a field after growth. If a means is found to immobilize the bacteria to grow isolated colonies, counts will be more accurate. Quantification is used to follow the progress of treatment and to correlate HBB levels with specific disease syndromes. Quantification is used also for antibiotic sensitivity measurements, comparing the level of growth with antibiotic treatment to the level of growth without treatment. Such antibiotic sensitivity measurements establish the basis for the clinical choice of antibiotic drugs.

In addition, ELISA may be performed with at least two purposes in mind—ELISA for detection of serum antibodies and an ELISA for quantification of organisms. ELISAs may be performed using whole, intact or disrupted HBB or one or more specific components of HBB prepared by purification or by recombinant production. Such components are bound to the wells of a plate or to another solid support. A dilution of the serum is incubated with the immobilized component attached to the solid support. The solid phase is washed and incubated with one or more secondary reagents ultimately linked to an enzyme that binds to the antibodies (immunoglobulins) in the serum. The solid support is treated with an enzyme substrate to produce a detectible and quantifiable reaction that is read with a spectrophotometer or similar instrument.

For quantitation, a solid support would be coated with disrupted bacteria or bacterial components including recombinant components, unmodified or modified, incubated with serum and then with a tagged anti-human immunoglobulin. An enzyme reaction would produce a quantifiable product. The level of antibodies in general, or the level of antibodies against specific bacterial components that correlate with specific disease entities are used to establish diagnosis for entities that are currently defined on the basis of their clinical presentations. For detection of serum antibodies, solid supports are coated with a specific antibacterial antibody and incubated with serum. This binds bacteria to the solid phase. The plate is incubated with tagged antibacterial antibodies and an enzyme reaction produces a quantifiable product Polyclonal and monoclonal antibodies are used in multiple ways. Antibodies are tagged in a variety of ways and used to identify organisms in tissues and to quantify directly organisms in fluids—including blood—for instance via laser flow cytometry, allowing faster and more accurate quantitation.

An additional technique well known in the art is the use of Western blots. In this procedure, disrupted bacteria are electrophoresed in a system such as SDS-PAGE, separating bacterial protein components in a reproducible manner. The proteins are blotted onto a suitable support, such as nitrocellulose or a nylon membrane, and incubated with serum. A tagged antihuman immunoglobulin is reacted with the blot and an enzyme reaction produces a visible product in areas of serum binding. The pattern of reaction is anticipated to correlate with specific diagnoses.

Probe-based tests directed against specific DNA or RNA sequences can be used both qualitatively and quantitatively. DNA or RNA probes are tagged and hybridized directly with nucleic acids extracted from samples, analogous to the use of antibodies above. DNA amplification methods such as PCR may be used to increase the sensitivity of the test to identify the presence of very low numbers of organisms. Southern and Northern blots are used routinely, and the probes may be attached to solid phases for automated screening. Specific probes and mutational analysis are used to identify specific strains that may have particular disease associations. Finally, any of the above methods can be packaged into a diagnostic kit for convenient use.

EXAMPLE 14

Uses of Engineered HBB

The whole HBB bacterium or components thereof also are used to create a vaccine, with modifications to make the bacterium sufficiently immunogenic. The procedures in Example 13, as well as a vaccine are employed using cloned or modified (engineered) proteins, DNA or RNA. As is known in the art, certain modifications have particular advantages in particular situations. Further, modified organisms are used to replace pathogenic strains in the body with strains that do not elicit disease-causing reactions, and to deliver a variety of genes or gene products (proteins) to an individual—both genes known to be defective or vaccine components, for immunogenic proteins associated with viruses.

Additionally, HBB is engineered to contain and express genes for therapeutically important gene products, including but not limited to hormones, growth regulators, antitumor antigens, antibodies, other therapeutic antigens, and interleukins. In so doing, HBB is engineered to transcribe, translate and process heterologous proteins. HBB also is engineered to respond to human effectors such as, e.g., serum or plasma glucose, alanine, and various hormones. Specifically, diseases where the toxic metabolite is accumulated in the plasma or serum are very effectively treated by engineered HBB. Further, suicide genes are inserted into HBB so that the bacterium may be destroyed when therapeutically effective to do so. One further facet of immunological use of HBB is to engineer HBB to produce the antigen of choice on its cell surface so as to provide continual boosting for the immune system.

The following references were cited herein.

1. Gerhardt, ed in chief, Methods of General and Molecular Bacteriology, American Society for Microbiology 1994.

2. Sonnenwirth, et al., Gradwohl's Clinical Laboratory Methods and Diagnosis, eighth edition. C. V. Mosby Co. 1980.

3. Lennette, Edwin H., ed in chief, Manual of Clinical Microbiology, 3rd ed. American Society for Microbiology, 1980.

4. Prophet, et al., eds, Laboratory Methods in Histotechnology. American Registry of Pathology 1992.

5. Hacker, et al., Molecular Microbiology (1997) 23 (6) 1089–1097. Nucleic Acid Techniques in Bacterial Systematics, Edited by E Stackebrandt and M Goodfellow, 1991, John Wiley and Sons.

6. Clinical and Pathogenic Microbiology, Howard, B. (Ed.) 1994, A. C. V. Mosby-Year Book, Inc.

7. Ludwig, et al., 1992, System. Appl. Microbiol. 15: 487–501.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. Isolated DNA consisting of a sequence selected from the group consisting of SEQ ID No: 1 and 3, wherein said DNA encodes a human blood bacterium ribosomal RNA in a normal individual's blood.

2. Isolated DNA consisting of a sequence selected from the group consisting of SEQ ID No: 2 and SEQ ID No: 4, wherein said DNA encodes a human blood bacterium ribosomal RNA in a diseased individual's blood.

3. The isolated DNA of claim 2, wherein said individual has a disease selected from the group consisting of chronic fatigue syndrome, multiple sclerosis, lupus erythematosis, rheumatoid arthritis and fibromyalgia.

4. Isolated DNA consisting of SEQ ID No: 5, wherein said DNA encodes an intergenic spacer region of a human blood bacterium.

5. An isolated DNA consisting of SEQ ID No: 6, wherein said DNA encodes a drug resistant protein of a human blood bacterium.

* * * * *